United States Patent [19]
Williams et al.

[11] Patent Number: 5,246,014
[45] Date of Patent: Sep. 21, 1993

[54] IMPLANTABLE LEAD SYSTEM

[75] Inventors: Terrell M. Williams, Coon Rapids; James L. Jula, White Bear Lake; James E. Upton, New Brighton, all of Minn.; Sten J. Ryden, Gothenburg, Sweden; Paul D. Blankenau, Minneapolis, Minn.

[73] Assignee: Medtronic, Inc., Minneapolis, Minn.

[21] Appl. No.: 790,605

[22] Filed: Nov. 8, 1991

[51] Int. Cl.$^5$ .............................................. A61N 1/05
[52] U.S. Cl. ....................................... 607/122; 607/9
[58] Field of Search ............... 128/784, 785, 786, 642, 128/419 P

[56] References Cited

U.S. PATENT DOCUMENTS

| | | | |
|---|---|---|---|
| 28,990 | 10/1876 | Hon et al. | 128/419 P |
| 3,333,045 | 7/1967 | Fisher et al. | 128/784 |
| 3,348,548 | 10/1967 | Chardack | 128/419 |
| 3,737,579 | 6/1973 | Bolduc | 128/419 |
| 3,750,650 | 8/1973 | Ruttgers | 128/419 P |
| 3,754,555 | 8/1973 | Schmitt | 128/419 |
| 3,769,984 | 11/1973 | Muench | 128/404 |
| 3,814,104 | 6/1974 | Irnich et al. | 128/419 P |
| 3,844,292 | 10/1974 | Bolduc | 128/419 P |
| 3,974,834 | 8/1976 | Kane | 128/419 P |
| 4,146,036 | 3/1979 | Dutcher et al. | 128/419 P |
| 4,320,764 | 3/1982 | Hon | 128/635 |
| 4,402,328 | 9/1983 | Doring | 128/785 |
| 4,402,329 | 9/1983 | Williams | 128/785 |
| 4,456,017 | 6/1984 | Miles | 128/772 |
| 4,467,817 | 8/1984 | Harris | 128/786 |
| 4,470,777 | 9/1984 | McCorkle, Jr. | 128/303 R |
| 4,602,645 | 7/1986 | Barrington et al. | 128/786 |
| 4,608,986 | 9/1986 | Beranek et al. | 128/786 |
| 4,624,266 | 11/1986 | Kane | 128/785 |
| 4,646,755 | 3/1987 | Kane | 128/785 |
| 4,886,074 | 12/1989 | Bisping | 128/785 |
| 4,943,289 | 7/1990 | Goode et al. | 606/1 |
| 4,964,414 | 1/1990 | Handa et al. | 128/784 |
| 4,967,766 | 11/1990 | Bradshaw | 128/785 |
| 4,972,847 | 11/1990 | Dutcher et al. | 128/785 |
| 4,998,917 | 3/1991 | Gaiser et al. | 128/419 P |

OTHER PUBLICATIONS

Scheiner et al., "A Study of the Fatigue Properties of Small Diameter Wires Used in Intramuscular Electrodes", Journal of Biomedical Materials Research, vol. 25, 1991 pp. 589–608.

Primary Examiner—William E. Kamm
Assistant Examiner—Scott M. Getzow
Attorney, Agent, or Firm—Michael J. Jaro; Harold R. Patton; Reed A. Duthler

[57] ABSTRACT

An implantable active fixation lead system which connects a source of electrical energy, such as a pacemaker, to the cardiac tissue. The lead system includes a lead, an introducer and a guide catheter. The lead has a small diameter lead body, and an active fixation device for engaging the cardiac tissue. The lead body has an overall straight, uncoiled configuration, and an outer diameter of about 13 mils. The lead body includes a plurality of infinitesimal, bio-compatible, bio-stable electrically conductive strands which are tightly bundled together in a cable-like fashion to form a single conductor. A dielectric bio-compatible insulation coating surrounds the conductor to provide an insulation layer between the conductor and the body environment. The fixation device includes a crank portion which engages the introducer.

The introducer is assembled to the lead and includes a coupler which engages the crank portion of the lead fixation device. The coupler includes a closely wound coil, and an elongated generally cylindrical tip engaging member having an aperture which acts as an entranceway for the lead fixation device. The coupler retains and firmly engages the lead crank portion, and controls its engagement to, and disengagement from the cardiac tissue. Furthermore, the coupler prevents the lead active fixation device for over-perforating the cardiac tissue.

A catheter is assembled to the lead and the introducer, for imparting stiffness and improved steerability to the lead.

27 Claims, 12 Drawing Sheets

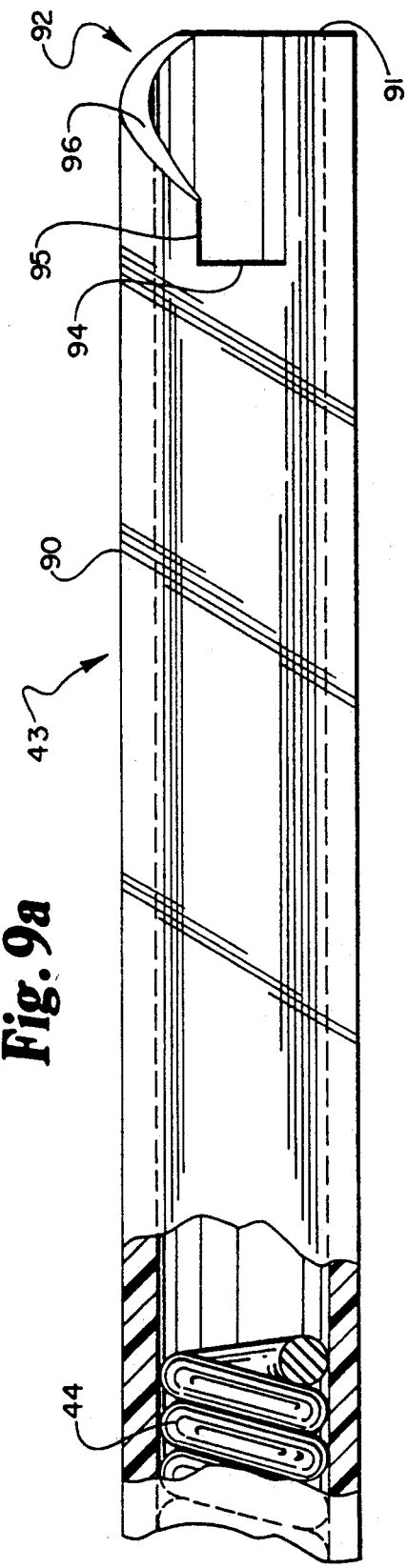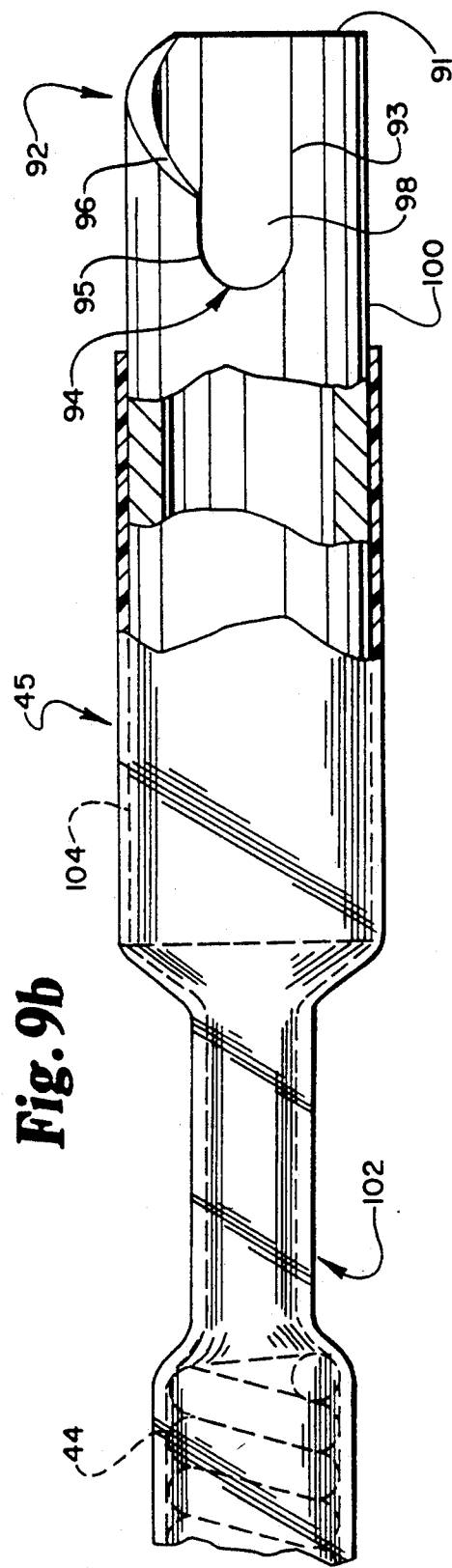

IMPLANTABLE LEAD SYSTEM

BACKGROUND OF THE INVENTION

1. Field of the Invention

The present invention relates generally to implantable cardiac leads, and more particularly to an active fixation lead system having a small diameter lead body and an introducer for improved maneuverability during implantation.

2. Background Art

An implantable intravascular lead assembly is oftentimes implanted for cardiac pacing, and comprises an electrical conductor which is adapted to be suitably connected to a source of electrical energy. The electrical conductor, in turn, includes an electrode tip which engages the endocardial tissue for stimulation and sensing. The lead assembly is intravenously inserted through a body vessel, such as a vein, into one or more cardiac chambers. The conductor is sealed from body fluids by a bio-compatible and bio-stable insulating material. A sheath is provided for improving the maneuverability of the conductor when inserted into, and guided through the veins for positioning in the heart chamber.

In a typical lead assembly, the electrode tip is firmly lodged in, and permanently secured to the endothelial lining of the heart. This lead assembly is referred to as an endocardial lead. Some examples of conventional endocardial leads may be found in the following publications: U.S. Pat. No. 3,348,548 to Chardack; U.S. Pat. No. 3,754,555 to Schmitt; U.S. Pat. No. 3,814,104 to Irnich et al.; U.S. Pat. No. 3,844,292 to Bolduc; and U.S. Pat. No. 3,974,834 to Kane. The teachings of these patents relate to various endocardial leads which are purportedly simple to manufacture and relatively easy to use by the operating physician.

The most desirable attributes of an endocardial lead are: (1) lead diameter and secure fixation of the electrode to the cardiac tissue to prevent electrode tip dislodgement; (2) implantation control with minimal damage to the vein, heart valve, cardiac tissue or other tissue that comes in contact with the lead, and for providing protection from over-perforation of the electrode through the cardiac tissue; and (3) removability.

A. LEAD SIZE AND ELECTRODE FIXATION

With increased patient's longevity, it has become common to replace the existing leads or to add new leads. The finite size of the vascular vessel through which the leads are passed cause a significant limitation to the number of leads that can be implanted in the same vessel. As a result, the dimensions of the lead body constitute a crucial factor in the success of the implantation procedure. In addition, when several conventional leads are implanted in the same vessel, they tend to frictionally rub against each other and to cause the dislodgement of the most recently implanted leads which have not yet fibrosed inside the heart. Furthermore, a lead having a large outside diameter tends to be relatively rigid and less flexible than a smaller sized lead, and also tends to have a higher electrical threshold and consequently a shorter pacemaker longevity. The greater the mass of foreign material, the more the risk of occlusive thrombosis and scar tissue formation and the more the risk of thrombotic pulmonary embolism. One of the biggest problems causing lead fracture today is crushing where the lead passes between the clavical and first rib. If the lead diameter is made small enough it can not be crushed by the minimum clearance presented between the clavical and first rib, thus eliminating this serious lead fracture problem.

The following patents are exemplary illustrations of conventional leads which use active or passive fixation methods, and which require a relatively large lead body to accommodate a stylet or a tip guidance device:

U.S. Pat. No. 4,146,036, issued to Dutcher et al., entitled "Body-Implantable Lead With Protector For Tissue Securing Means", and assigned to Medtronic, Inc., discloses an implantable endocardial lead 10 having a screw-in tip 42 for fixation to the endocardial tissue. The unipolar lead has a closely wound, coiled conductor 14 in the form of a spring spirally wound about and along the axis of the conductor 14. The conductor 14 is hollow and is adapted to receive a stiffening stylet 20 that extends through most of the length of the lead 10.

The stylet imparts rigidity to the lead body, facilitates its manipulation through the vein, the tricuspid valve and the right ventricle of the heart. After the lead is properly positioned inside the heart chamber, the stylet is rotated and causes the distal end 46 of the helical tip 42 to be lodged into the endocardial and myocardial tissues.

A significant limitation to the patented lead is the relatively large size of the lead body necessary for accommodating the stylet.

U.S. Pat. No. 4,886,074, issued to Bisping and entitled "Implantable Lead Assembly With Extendable Screw-In Electrode", discloses an endocardial lead which is manipulated by a stylet inserted therewithin. The lead includes a fixation device with a protected helical screw. The screw is released and advanced into the myocardial tissue by axial movement of the stylet.

Similar to the Dutcher U.S. Pat. No. 4,146,036, a significant limitation to the patented lead is the relatively large size of the lead body needed for accommodating the stylet or the tip guidance device, and to provide torque (coil) and counter torque (lead body) to extend the screw.

U.S. Pat. No. 4,402,329, issued to Williams, entitled "Positive Anchoring A-V Lead" and assigned to Medtronic, Inc., describes a single pass atrial-ventricular transvenous pacing lead where the atrial branch has an active fixation device and the ventricular branch has a passive fixation device. The lead is bifurcated at a point near or above the superior vena cava during normal transvenous insertion. The atrial and ventricular atrial border branches are positioned using a stylet.

Similar to the Dutcher U.S. Pat. No. 4,146,036 and the Bisping U.S. Pat. No. 4,886,074 above, a significant limitation to the patented lead is the relatively large size of the lead body which accommodates the stylets.

U.S. Pat. No. 4,402,328, issued to Doring and entitled "Crista Terminalis Atrial Electrode Lead", is another illustration of the use of a stylet during the implantation procedure. More particularly, this patent describes using the stylet for temporarily straightening the J-shaped section 14 of the atrial lead during implant. The lead tip includes tines, a passive fixation device, which are lodged in the right atrial appendage.

As with the other conventional leads, using the stylet it requires a larger lead body.

U.S. Pat. No. 4,967,766, issued to Bradshaw and entitled "Implantable Endocardial Lead With Fixation Apparatus Retractable By A Lanyard", is yet another illustration of the state of the art in implanting endocardial leads. The fixation device used in the lead 12 includes a sharpened helix 40 which can be retracted within an electrode. The lead includes a lumen 28 through which a stiffening stylet 62 can be inserted during implantation.

The Bradshaw patent is yet another reminder that the state of the art in the lead technology relies on stiffening stylets for maneuverability during implantation. These stylets significantly contribute to the augmentation of the lead diameter.

The following publications are exemplary illustrations of conventional leads which attempted to reduce the lead size and to address the concerns associated with the reduced dimensions:

U.S. Pat. No. 4,964,414, issued to Handa et al. and entitled "Electrode For Use In Implanting In A Living Body", relates to a lead 20 for implantation in the body. The lead includes a core 21 made of a plurality of infinitesimal wires 22. The core of the lead is arranged along the axial direction, and is coated with a biocompatible resin material. The core is coiled and is enveloped in a spirally coiled element 24 to impart flexibility to the lead.

While this lead appears to have a small outer diameter, the patent does not teach practical ways for using it as a pacing lead. There is no disclosure of method for affixing the lead electrode to the cardiac tissue, nor is there a teaching of a method for implanting the lead intravenously. The overly flexible nature of the lead does not allow it to be introduced in the vascular system without a stiffening guidance device. Furthermore, there is no disclosure of a method or device that allows the miniaturized lead to be connected to a universal pacemaker connector such as an IS-1 connector block.

The article entitled "A Study of the Fatigue Properties of Small Diameter Wires Used in Intramuscular Electrodes" by A. Scheiner et al., published in the Journal of Biomedical Materials Research, Vol. 25, 589–608 (1991), reviews material hardness, deformities and fatigue tests conducted on single and multi-strand wires used in intramuscular electrodes. Similar to the Handa patent above, the article suffers from incompleteness in that it does not disclose affixation, implantation and connection techniques for pacing purposes.

U.S. Pat. No. 4,467,817, issued to Harris and entitled "Small Diameter Lead With Introducing Assembly", relates to what is referred to as "small diameter" carbon fiber lead with an introducing assembly. The lead includes a multifilament, small diameter carbon lead body 12 surrounded by a stiffening sheath 14. The lead body has a diameter of approximately 0.053 inch which corresponds to a French 4 diameter. The sheath slides over the lead body and has a diameter corresponding to a French 5 diameter.

The sheath serves merely as an aid in guiding the lead through the vascular system to the target organ, and it is removed once the lead is positioned in its final destination. The sheath cannot be removed by sliding it off the lead body, but is rendered removable by providing it with separating grooves 34, which allow the sheath to be peeled apart.

While the patent describes the lead as a small diameter lead, the specification clarifies the actual dimensions of the lead and the introducing sheath, namely about 4 and 5 French diameters respectively. These dimensions do not qualify the lead as a miniaturized lead, since the diameters of several conventional leads range between 4 to 8 French. An example of such conventional leads is Model 4023 (4 French lead body), sold by Medtronic, Inc. Furthermore, the lead tip has a passive fixation device such as tines, and consequently does not provide for means to rotate the lead body to get the tip to be actively affixed endocardially.

U.S. Pat. No 4,608,986, issued to Beranek et al. and entitled "Pacing Lead With Straight Wire Conductors", represents an attempt to minimize the thickness of the lead body by using straight conductor wires. The lead body 12 is provided with a stylet receiving opening 18 and two connector fingers 20 and 22. The lead body is circular in cross-section and is made of a soft pliable material. It has a central lumen 50 and four conductor lumina 51–54 which are equally spaced apart from the central lumen.

The outer diameter of the lead body which remains implanted in the patient's vascular system is approximately 0.052 inch, that is in the range of 4 French diameter. As mentioned above, the 4 French diameter does not presently qualify as a miniaturized lead, and it would be desirable to design a lead having smaller dimensions.

While the above publications teach various ways for reducing the overall size of the lead, it is still desirable to design a smaller size lead, in the range of 1 or 2 French diameter, which uses temporary tools for implantation other than the conventional stiffening stylet. Furthermore, the conventional leads described in these publications use active fixation devices, such as helical screw-in tips, and have met with varying degrees of success with respect to implantation control and protection against perforation of the cardiac tissue.

B. IMPLANTATION CONTROL AND TOOLS PROTECTION FROM OVER-PERFORATION

Another desirable attribute of an endocardial lead is the ease of implantation and the accuracy of lead tip control during the implantation procedure. Implantation control involves the proper and prompt implantation as well as the accurate and safe positioning of the lead in its final placement position.

Implantation control is a significant factor in reducing risks to the patient, associated with the invasive implant procedures. Proper implantation control minimizes the implantation time during which the patient, the physician and the medical staff are exposed to radiation resulting from fluoroscopic X-rays, thus resulting ultimately in a more efficient and less costly health care system.

The following patents are exemplary illustrations of conventional leads and tools which attempted to address the implantation control issues:

U.S. Pat. No. 4,456,017, issued to Miles and entitled "Coil Spring Guide With Deflectable Tip", discloses an angiographic coil spring guide with a deflectable tip for better maneuverability during the insertion of the catheter into the body vessel. The guide includes a coil spring 14 extending the length of the coil spring, and a head member 20. A core wire extension 18 connects the distal end of the core wire to the head member, such that rearward movement of the core wire causes the head member to deflect outwardly.

Although this catheter manipulation technique appears to be simple, it has yet to be adapted to endocardial leads, and particularly those with an active fixation device, which require an apparatus for imparting torque to the fixation device for lodging the lead tip into the cardiac tissue.

U.S. Pat. No. 3,769,984, issued to Muench and entitled "Pacing Catheter With Frictional Fit Lead Attachment", discloses the use of a catheter 10 with a frictional fit lead attachment in cardiac pacing. The catheter includes a dielectric, flexible tubular element 11 suitable for transvenous insertion. A first electrode 12 is provided at the distal end of the tubular element, and a second electrode 14 is provided and is spaced rearwardly from the first electrode 12. Two conductors 15 and 17 connect the electrodes to a pacemaker. Conductors 15 and 17 include stranded wires of highly flexible, small diameter metal filaments of less than 50 microns in diameter. The patent teaches twisting the filaments such as with conventional twists of approximately 5 turns per inch. The catheter may include an axial lumen which allows a stylet to be extended therethrough for manipulation during implantation.

The patent also states that any suitable method of effecting the connection may be employed, but it does not teach how to connect the two small diameter conductors 15 and 17 to a standard pacemaker connector configuration known as the IS-1 connector block.

It is noteworthy to indicate that the purpose of miniaturizing the conductors 15 and 17 may arguably have been defeated by the relatively large diameter of the catheter, i.e., 0.0500 inch diameter, particularly that the conductors are fixedly secured and undetachable from the tubular element 11. In addition, the catheter permits "floating" insertion into the heart and does not appear to have been designed to accommodate any fixation means, and particularly not an active fixation assembly which generally requires rotation of the tip, i.e., helical screw, for attachment to the cardiac tissue.

U.S. Pat. No. 4,998,917, issued to Gaiser et al. and entitled "High Torque Steerable Dilatation Catheter", relates to a steerable dilation vascular catheter 10 which is particularly adapted for angioplasty procedures. The catheter includes a core wire 13 disposed within an inner lumen 14 with a flexible coil 15 on the distal portion thereof and an inflatable relatively inelastic balloon member 16. An arm 24 is adapted to receive the proximal end of the core and has a torquing knob 25 in order to rotate the core within the lumen, and thus to rotate the distal portion thereof.

The patented catheter, is similar to the catheter disclosed in the Muench 3,769,984 patent above, with respect to the non- availability of fixation means, and means for preventing over-perforation of the cardiac tissue.

U.S. Pat. No. 4,602,645, issued to Barrington et al. and entitled "Atrio-Ventricular pacing Catheter", relates to an atrio-ventricular pacing catheter assembly which includes a main guiding catheter and a pair of electrical leads adapted to make electrical contact with the ventricle and atrium of the patient. The guiding catheter has a pair of lumens which guide and contain the atrial and ventricular leads.

The guiding catheter is left implanted in the patient's body even after the leads are secured in place. Consequently, the patented guiding catheter does not solve the problems with relatively large lead dimensions, but rather substantiates the conventional standard and its inability to effectively reduce the pacing lead size.

U.S. Pat. No. 4,972,847, issued to Dutcher el al. and entitled "Pacing Lead And Introducer Therefor", relates to a pacing lead installation tool known as the introducer 20. The introducer holds the lead 21 prior to implantation of a helical electrode into the myocardium. The introducer includes a pair of side-by-side elongated beams 37 and 38 which are pivotally connected together for housing a portion of the lead, and for holding the electrode.

However, the introducer seems to have a rigid construction which is not adaptable for use in intravenous implantation.

U.S. Pat. No. 4,646,755, issued to Kane and entitled "Introducer Tool For Endocardial Screw-In Lead", relates to an introducer tool 10 for a helical screw-in endocardial lead 11. The introducer tool includes an elongated plunger housing 12 which is slidably positioned within an elongated locking tube 13. A stylet 14 is inserted through a lumen in the lead body for stiffening it during implantation. The lead is rotated relative to the introducer tool about the stylet to fix the helix screw-in assembly of the lead.

As discussed above, the use of the stylet contributes a larger outer diameter of the lead in order to accommodate the stiffening stylet. In addition to the lead size, the patented introducer tool does not protect from over-perforation of the cardiac tissue.

U.S. Pat. No. 4,624,266, issued to Kane and entitled "Introducer Tool For Screw-In Lead", discloses yet another example of the conventional introducer tools used in the implantation of screw-in leads. The patent describes a stylet and an introducer, such that the stylet has a knob at its proximal end and extends through the introducer tool and coiled conductor of the lead to engage a helix assembly positioned within the electrode of the lead. The stylet urges the helix assembly into contact with the cardiac tissue. The knob of the stylet engages the introducer tool to lock the stylet to the introducer tool and to permit the screw-in lead to be rotated around the stylet to cause the helix assembly to penetrate the cardiac wall.

Once again, the use of a stylet to help in the stiffening and guiding of the lead during implantation seems to be the prevalent technology. Additionally, the present patent is similar to the Kane 4,646,755 patent described above, in that it does not teach a technique to avoid over-perforation of the cardiac wall.

U.S. Pat. No. 4,320,764, issued to Hon and entitled "Fetal Electrode" illustrates a lead for use in measuring the change in pH values of a fetus. The lead includes a holder 10 made of insulating material, and a spiral electrode extending from the forward end of the holder, and adapted to engage the fetus during delivery. A maternal electrode includes a rear fin 23 integrally formed with the holder 10 and engages slots 24 of the driving tube 22 to enable the doctor to rotate the electrode assembly.

U.S. Pat. No. 4,827,428, issued to Hon and entitled "Bipolar Electrode Structure For Monitoring Fetal Heartbeat And The Like", describes an electrode assembly for monitoring fetal heartbeat. The electrode assembly includes a curved guide tube adapted to be inserted through the vagina and cervix of a woman in labor. A retaining coil is mounted on a holder member which is slidably disposed in the guide tube. A flexible driving tube is adapted to rotate the holder member to screw the retaining coil into a fetal epidermis and two spaced electrodes. Driving connection between the holder member and the flexible driving tube is provided by slots in the forward end of the driving tube and fins on the holder.

U.S. Pat. No. 3,750,650, issued to Ruttgers and entitled "Double Spiral Electrode for Intra-Cavity Attachment", relates to an electrode device for obtaining ECG signals from a fetus. The electrode device includes two spiral pointed catcher elements displaced by 180 degrees and mounted in an insulating carrier 18. The carrier is mounted on a guiding tube 20 which is split at its upper end so that the conical tube parts 20' thus formed surround the carrier 18. Column 3, lines 24 through 27, and FIG. 2.

U.S. Pat. No. 3,737,579, issued to Bolduc, entitled "Body Tissue Electrode And Device For Screwing The Electrode Into Body Tissue", and assigned to Medtronic, Inc., relates to a body implantable lead having a flexible insulated conductor adapted for connection to a power supply, and a distal end adapted for attachment to a body tissue. FIGS. 2 and 3 illustrate a tool 40 used in conjunction with the lead to facilitate the screwing of an electrode 18 into the body tissue. The tool 40 includes a substantially cylindrically-shaped member having a longitudinal axis 42, and axial slot 48. The slot 48 is shaped in such a way to conform to and engage ribs 25 of raised portion 24 of the lead 10. This patent is incorporated herein by reference.

U.S. Pat. No. 3,844,292, issued to Bolduc, entitled "Intravascular Lead Assembly", and assigned to Medtronic, Inc., teaches a body-implantable, intravascular lead assembly which is adapted to be connected to a source of electrical energy. A conductive barb is secured to the distal end of the lead. FIG. 2 shows a cross-sectional view of a device 30 used to position the lead 10. The device 30 has a pair of concentric, substantially cylindrical hollow tubes 32 and 34. The outer tube 32 is maintained in a fixed position. The inner tube 34 is axially movable within outer tube 32 and sleeve 38. The lead is positioned in the opening defined by the opening defined by the inner tube 34 and the opening 44 in plunger 42. Pin 52 projects from one end of a slide 50 and is positioned in the aligned openings in sleeve 38 and plunger 42. This patent is incorporated herein by reference.

The foregoing U.S. Pat. Nos. 4,320,764, and 4,827,428 to Hon; 3,750,650 to Ruttgers; and 3,737,579 and 3,844,292 to Bolduc describe various tools and methods for controlling the introduction of an electrode assembly, and for securing it to a body tissue.

However, it is apparent that the state of the art technology does not satisfactorily provide for adequate protection against over-screwing of the lead into the cardiac wall, nor does it support the use of small diameter leads. These conventional leads use guiding catheters which are left in the body vessel after implantation, and which increase the size of the leads. An apparent disadvantage of the conventional introducer tools is that they are not equipped to dislodge the screw-in electrode from the cardiac tissue for better positioning of the lead during or shortly after the implantation, safely and without causing significant damage.

C. REMOVABILITY

Yet another desirable attribute of an endocardial lead is the ease of its removability during and shortly after implantation. The following patents provide a brief background of conventional leads which are claimed to be extractable with minimal damage to the body tissue:

U.S. Pat. No. 4,471,777, issued to McCorkle, Jr. and entitled "Endocardial Lead Extraction Apparatus And Method", describes a composite assembly having three concentric catheters. The first catheter grasps onto the lead, and the second catheter is rotated to cause a smooth tapered leading edge to separate scar tissues. The third catheter is rotated to dislodge the lead tip from the heart tissue. The lead is then supposedly removed from the heart via the venous path without excessive force to the cardiac wall.

While the above extraction apparatus can conceptually be used, its practical viability remains to be proven. The complexity and size of the apparatus, as well as the scarring remaining from the extraction procedure, have not been satisfactorily addressed by the patent. Furthermore, the patented extraction tool deals with chronic removal of the lead and causes scarring to the cardiac tissue.

U.S. Pat. No. 4,943,289, issued to Goode et al. and entitled "Apparatus For Removing An Elongated Structure Implanted In Biological Tissue", relates to an apparatus for removing an implanted lead. The apparatus includes a flexible stylet with an expandable wire coil attached to the distal end for securing the distal end of the stylet to the lead.

The removal apparatus seems to be designed for use in conjunction with a conventional lead having a lumen to accommodate the stylet at the expense of the lead size.

Consequently, while lead removal devices have been proposed, they are not ideal because they do not allow for better positioning of the lead during and after the implantation, safely and without causing significant damage to the cardiac tissue.

The above cited patents and publications have attempted, with varying degrees of success, to provide endocardial leads with some of the desirable features without the attendant problems or undesirable characteristics as described above.

SUMMARY OF THE INVENTION

It is therefore a principal object of the present invention to provide adequate solutions to the above concerns of conventional lead systems.

Another object is to provide a small diameter lead body to reduce scar tissue formation and occlusion of the venous system through which the lead passes, to reduce thrombo-embolisms, and to provide an active fixation device and an introducer for improved maneuverability during implantation.

Another advantage is to provide a small diameter lead body that will fit the clearance between the clavical and first rib to prevent crush fracture, the biggest cause of lead fracture with available leads.

Another object is to provide a lead system that uses a catheter introducer for manipulating and guiding the small diameter lead during implantation, repositioning and explantation.

Yet another object is to teach a method for implanting the small diameter lead and for affixing the lead tip to preselected points or target in the cardiac wall.

A further object is to disclose an introducer tool and lead tip which protect against over-perforation of the cardiac wall. The perforation depth of the screw is automatically limited to ensure adequate perforation depth to provide good pacing and fixation.

An additional object is to provide a lead system that allows accurate and safe positioning of the lead, and which is capable of being repositioned and explanted during and shortly after implantation, without excessive scarring to the heart tissue.

An additional object is to provide a connector block for electrically and mechanically coupling the small size lead to an electrical source of energy, such as a pacemaker.

Briefly, the above and further objects and features of the present invention are realized by providing a new implantable active fixation lead system which connects a source of electrical energy, such as a pacemaker, to the cardiac tissue. The lead system includes a lead, an introducer and a guide catheter. The lead has a small diameter lead body, and an active fixation device for engaging the cardiac tissue.

The lead body has an overall straight, uncoiled configuration, and an outer diameter of about 0.0130 inches. The lead body includes a plurality of infinitesimal, bio-compatible, bio-stable electrically conductive strands which are tightly bundled together in a cable-like fashion to form a single conductor. A dielectric bio-compatible insulation coating surrounds the conductor to provide an insulation layer between the conductor and the body environment. The fixation device includes a crank portion which engages the introducer.

The introducer is assembled to the lead and includes a coupler which engages the crank portion of the lead fixation device. The coupler includes a closely wound coil, and an elongated generally cylindrical tip engaging member having an aperture which acts as an entranceway for the lead fixation device. The coupler retains and firmly engages the lead crank portion, and controls its engagement into, and disengagement from the cardiac tissue. Furthermore, the coupler prevents the lead active fixation device from over-perforating the cardiac tissue.

A catheter is assembled to the lead and the introducer, for imparting stiffness and improved steerability to the lead.

The above objects of the present invention are also realized by the new method of assembling and using the lead system. The assembly method includes the steps of inserting the lead body inside, and pulling it through the introducer. The introducer is then rotated until the crank portion penetrates the aperture and is retained thereby, such that a torque applied to the proximal end of the introducer is imparted almost entirely to the lead fixation device. The lead-introducer assembly is then inserted inside the catheter.

During the implantation procedure, the lead fixation device is kept recessed within the catheter to prevent contact with, and damage to the body. When the catheter is satisfactorily positioned, the introducer is pushed forward, to expose the screw-like tip of the lead active fixation device, and to force it into contact with the cardiac tissue. The introducer is rotated clockwise to cause the lead tip to engage the cardiac tissue.

The lead system prevents the active fixation device from over-perforating the cardiac tissue, by causing the crank of the lead tip to ride on a coupler ramp as the tip is screwed deeper into the cardiac tissue. As the crank disengages from the coupler, the tip is prevented from advancing further into the cardiac tissue, regardless of continued rotation of the introducer.

Threshold tests are conducted for confirming the proper positioning of the lead. If further adjustments are needed, the lead is disengaged from the cardiac tissue, by pushing the introducer forward so that the coupler re-engages the crank, and by rotating the introducer in the counterclockwise direction for gradually disengaging the lead from the cardiac tissue.

Upon proper positioning of the lead and completion of the threshold tests, the catheter and the introducer are retracted from the lead, and the lead body is cut to length and connected to the pacemaker via a modified standard connector.

The present lead system and method of assembling and using it have therefore successfully addressed and resolved the concerns associated with conventional leads. The simplicity of the lead body reduces the overall manufacturing cost of the lead, and makes the lead system readily available for a broad range of medical applications.

The lead system is easily and accurately maneuverable during implantation, and uses an introducer tool which provides precise electrode depth control automatically and protects the lead from over-perforation of the cardiac wall. In addition, the lead system is capable of being repositioned and explanted during and shortly after implantation, without excessive scarring to the venous system or the heart tissue.

BRIEF DESCRIPTION OF THE DRAWINGS

The above and other options, features and advantages of the present invention will become more apparent from the following more particular description thereof, presented in conjunction with accompanying drawings, wherein:

FIG. 9a is a greatly enlarged side elevational view of a coupler forming part of the introducer of FIG. 2, with portions thereof cutaway;

FIG. 9b is a greatly enlarged side elevational view of an alternative coupler, with portions thereof cut away;

FIG. 14 is an enlarged detail view of a crank portion forming part of the lead tip, shown in engagement with the coupler of FIG. 9a;

DESCRIPTION OF THE PREFERRED EMBODIMENT

Figure 1:
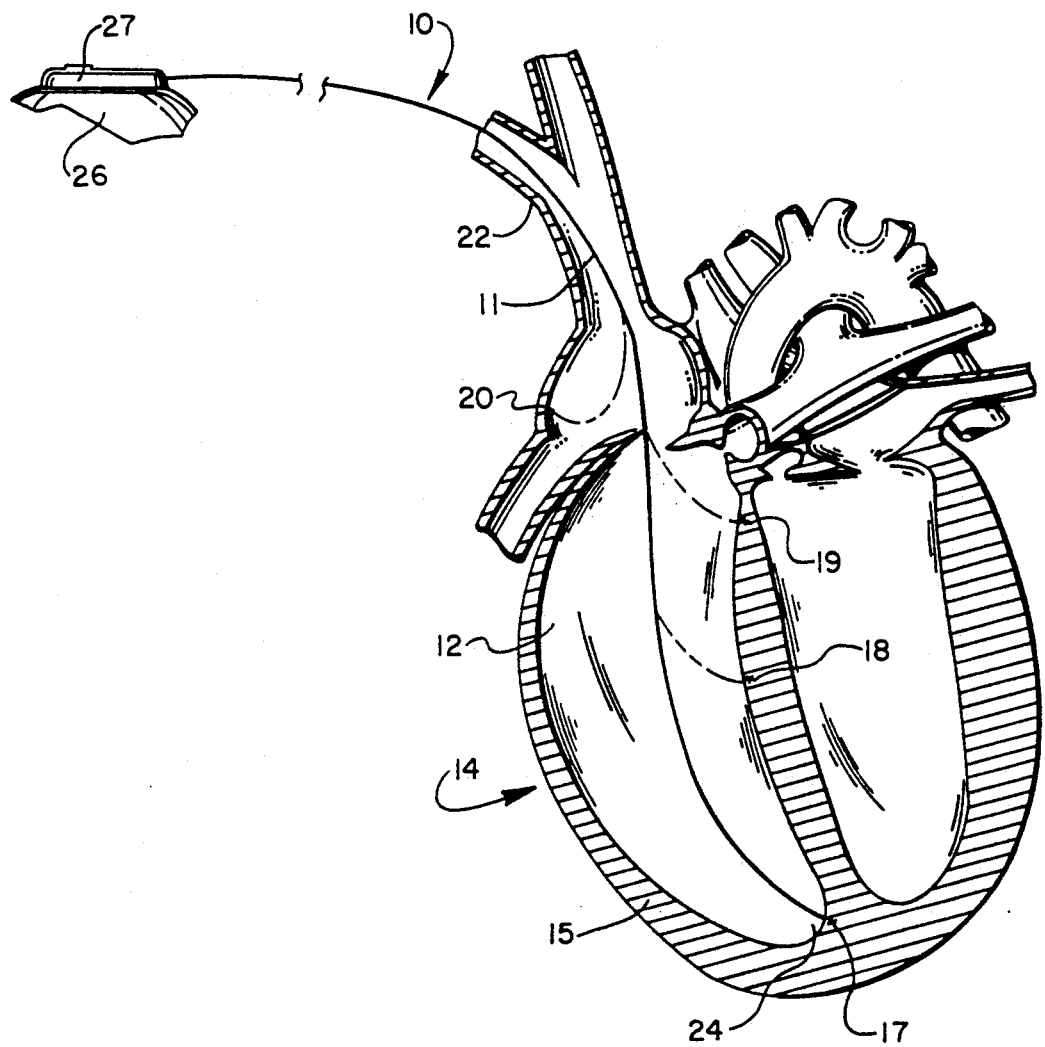
FIG. 1 is schematic sectional view of a human heart with an intra-vascular lead of the present invention implanted in various locations in the atrial and ventricular chambers.

Referring now to the drawings and more particularly to FIG. 1 thereof, there is illustrated an intra-vascular lead 10 which is constructed according to the present invention and which is implanted in the right ventricular chamber 12 of the human heart 14. The lead 10 has a substantially small outer diameter ranging from about 0.75 French to 2 French. The lead 10 replaces conventional leads, and, as illustrated, it can be secured to the cardiac wall 15 at various locations 17, 18, 19 and 20 in the ventricular chamber 12 or the atrial chamber 16.

The lead 10 includes a lead body 11 which is inserted in the patient's heart 14 through a vessel 22 the subclavian vein. The lead 10 includes, at its distal end, a screw-in type helical tip or electrode 24 which engages the endocardial and myocardial tissues for stimulation and sensing of cardiac events. The proximal end of the lead 10 is coupled to a pacemaker 26 by means of a connector block 27.

LEAD BODY SIZE

An important aspect of the present invention is the small outer diameter of the lead body 11. The preferred outer diameter of the lead body 11 is approximately 0.013 inches (one French), and typically ranges between 0.010 inches and 0.026 inches for unipolar leads. It should however become apparent to those skilled in the art after reviewing the present disclosure, that the outer diameter of the lead body 11 can vary with the nature of the application, the material composition and number of infinitesimal conductors forming the lead body 11, and the type and thickness of the insulation coating which envelops these conductors.

The lead body 11 has a straight, uncoiled configuration with high flexibility and longevity. This allows the lead 10 to withstand the severe conditions to which it will be subjected, without significant failures, cracking or breaking occurring over its expected useful life. The lead 10 permits the implantation of significantly more leads than conventionally possible, in view of the finite size of the vessel 22. By using the lead 10, it is now possible to implant several adjacent leads in the vessel 22. As a result, this increased lead density presents a significant improvement over conventional leads. Additionally, the small surface area and volume of the lead body 11 minimizes friction between adjacent leads. The small diameter fits within the clearance of the clavical and first rib to prevent lead crushing and fracture.

LEAD SYSTEM; LEAD, INTRODUCER AND CATHETER

Figure 2:
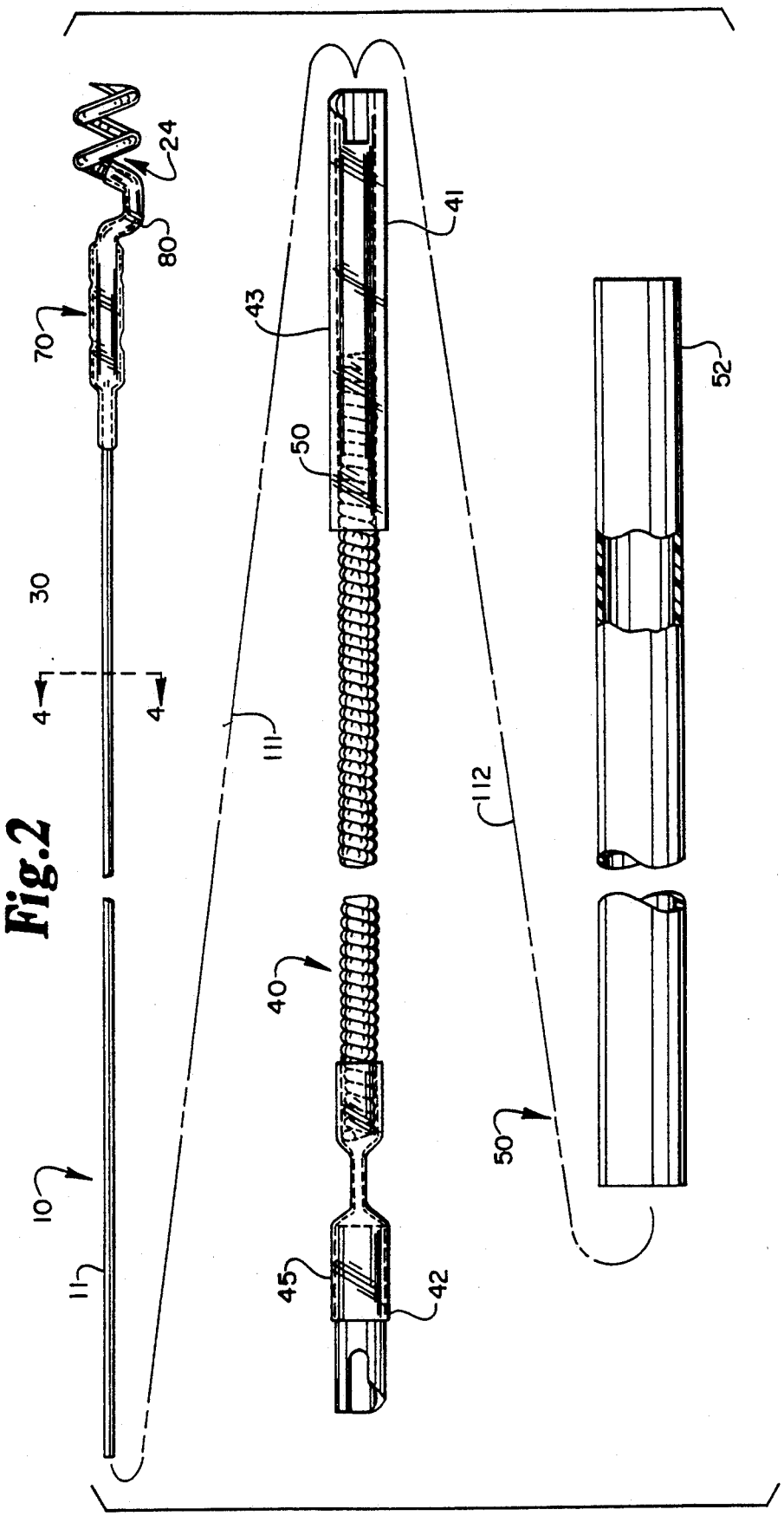
FIG. 2 is an exploded side elevational view of a lead system of the present invention showing the lead of FIG. 1, an introducer which slides over the lead, and a catheter which slides over the introducer.

Referring now to FIG. 2, there is illustrated an exploded view of a lead system 30 which comprises the lead 10. It should be appreciated that the small diameter and high flexibility of the lead 10 render it too pliable for implantation without a stiffening device. The lead system employs a novel device, referred to as the introducer 40. The introducer 40 differs from the conventional stylet in that it eliminates the need for an axial lumen within the lead body, which, as discussed above, increase the outer diameter of the lead body. Therefore, by using the introducer 40, it is now possible to significantly reduce the size of the lead body 11.

The introducer 40 fits over the lead body and a catheter 50, in turn, fits over the introducer 40. As further illustrated in FIG. 3, the distal end 41 of the introducer 40 engages the tip 24 of the lead 10 causing it to rotate and engage the cardiac wall 15. The catheter 50 guides the introducer-lead assembly 30-10 through the venous system during implantation.

In use, the lead system 30 is first assembled by sliding the introducer 40 over the lead body 11 until the distal end 41 of the introducer 40 firmly engages the screw-in tip 24, such that a rotational torque imparted to the proximal end 42 of the introducer 40 is transmitted almost entirely to the tip 24. The catheter 50 houses the introducer 40 and the lead 10, and has sufficient torsional stiffness for steerability.

During implantation, the tip 24 is recessed entirely within the catheter 50 to prevent contact with, and damage to the vessel 22 or the endocardial surface of the heart. The introducer 40 is longer than the catheter 50 such that during implantation, the proximal end 42 of the introducer 40 protrudes outside the catheter 50, to facilitate grasping and manipulation of the introducer-lead assembly 40-10. When the distal end 52 of the catheter 50 reaches its approximate final placement position, the introducer 40 is pushed forward and the tip 24 is exposed and forced into contact with the cardiac wall 15.

Whereupon, the introducer 40 is rotated clockwise for causing the tip 24 to be screwed into the cardiac wall 15. As the tip 24 is screwed deeper into the cardiac wall 15, it is pulled away from the distal end 41 of the introducer 40 until it is completely disengaged therefrom. As will be described later in greater detail, when the tip 24 is disengaged from the introducer 40, it can no longer be screwed further into the cardiac wall 15, regardless of the continued rotation of the introducer 40, thus providing protection from over-perforation.

When the tip 24 is lodged in the cardiac wall 15, threshold tests are conducted to determine whether the lead 10 is properly placed. If adjustments are needed, the introducer 40 is advanced forward in contact with the tip 24, and is rotated counterclockwise for causing the distal end 41 to re-engage the tip 24. This counterclockwise rotation will disengage the tip 24 from the cardiac wall 15. The tip 24 is repositioned and the threshold tests are repeated.

Upon proper positioning of the lead 10, the catheter 50 and the introducer 40 are drawn back and retracted from the lead 10. The lead 10 is cut to length and connected to the pacemaker 26 via the standard connector block 27.

While the lead system 30 will be described in connection with a small diameter lead body 11, it should be appreciated that the lead system 30 can alternatively be used in conjunction with a conventional lead for dual chamber pacing.

DESCRIPTION OF THE LEAD

Referring now to the drawings and more particularly to FIGS. 2, 4, 5, 6, 7 and 8 thereof, the lead 10 will now be described in detail. As better illustrated in FIGS. 2 and 4, the lead 10 of the present invention includes a pacing lead body 11 of minimal diameter, and contains several twisted but uncoiled conductive strands 32-38 which are constructed and arranged to significantly reduce the flex fatique failure rate of the lead 10 and to reduce its outer diameter.

This is achieved by providing the lead body 11 with a conductor 60 and a protective insulation coating 61. The conductor 60 includes the strands 32-38 which are made of electrically conductive filaments. In the preferred embodiment, the conductor 60 is composed of six peripheral strands 32-37 which are arranged around a central strand 38. It should however be understood that a different number of strands can be used to form the conductor 60 of the present invention.

The strands 32-38 are stranded together using a conventional stranding machine to cause them to be tightly bundled in a cable-like fashion to form the unitary conductor 60. The lay or pitch of the stranding varies typically between 0.30 inch and 0.60 inch. The strands 32-38 have similar material composition and shape, and hence, for reasons of brevity only the strand 37 will be described below in greater detail.

The preferred cross-sectional shape of the strand 37 is circular, with a diameter of 0.0020 inch for the seven-strand conductor 60. This diameter can range between 0.0005 inch and 0.0030 inch, depending on the material composition and outer diameter of the conductor 60. It should be however understood that other cross-sectional shapes of the strand 37 can be used.

The outer diameter of the conductor 60 typically ranges between 0.0030 inch and 0.0130 inch, and has a preferred value of 0.0060 inch. It should however become apparent to those skilled in the art that the outer diameter can exceed 0.0130 inch. The length of the lead body 11 varies with patient size and selected implant or insertion site.

The strand 37 is made of bio-compatible and bio-stable electrically conductive material such as MP35N, or other material that is fatigue and corrosion resistant. To enhance fluoroscopy visibility of the lead body high density material, such as platinum or platinum alloys, is used.

Figure 4:
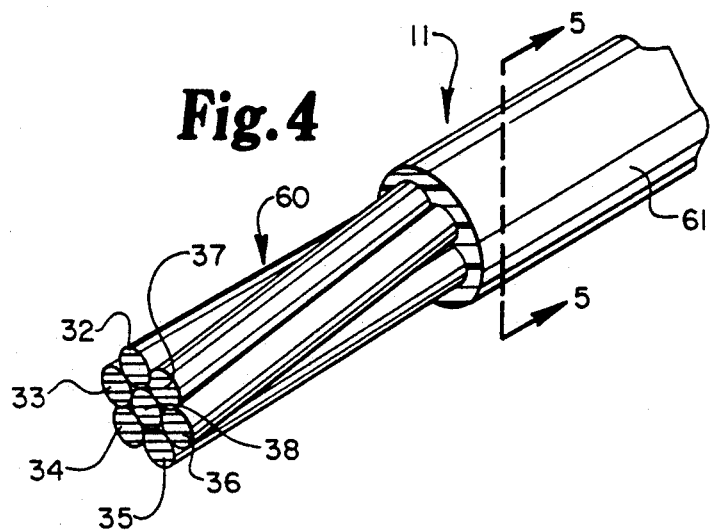
FIG. 4 is a greatly enlarged isometric cross-sectional fragmentary view of the lead of FIG. 2 taken along line 4—4.

The insulation coating 61 will now be described in greater detail in relation to FIGS. 4, 5 and 6. The coating 61 is made of dielectric fluoropolymer material which is bio-compatible, bio-stable, abrasive resistance, flexible and tough. As illustrated in FIG. 4, the coating 61 is formed over the conductor 60 in an even manner for producing a smooth outer surface of a generally circular outer diameter.

Consequently, the lead body 11 has an overall straight linearized uncoiled configuration that results in a reduction of the lead body outer diameter, as well as a reduction in the electrical resistance and length of conductor wire needed to form the lead body 11 as compared to the commonly used coil. Thus, significant cost reduction is achieved, which results in a more efficient and attainable health care system. For instance, in certain applications, i is now possible to reduce the conductor cost by a factor of over 25 times.

Figure 5:
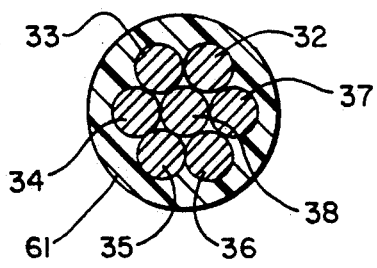
FIG. 5 is a cross sectional view of the lead body of FIG. 4 taken along line 5—5.

Referring now to FIG. 5, there is illustrated a cross-sectional view of the preferred embodiment of the lead body 11 taken along line 5—5 in FIG. 4. The insulation coating 61 is formed tightly around the conductor 60 to provide an insulation layer between the conductor 60 and the body environment. The conductor 60 is centered at about the geometric axis of symmetry of the insulation coating 61, in order to obtain maximum insulation characteristics around the entire conductor 60. Otherwise, if the conductor 60 were eccentrically located with respect to the coating 61, the probability of electrical leakage through the coating 61 is increased, and protection from physical damage is decreased. Therefore, it is now possible to design a lead body 11 having an outer diameter of about 0.0100 inches. The outer diameter of the lead body 11 can also be enlarged with varying applications.

Figure 6:
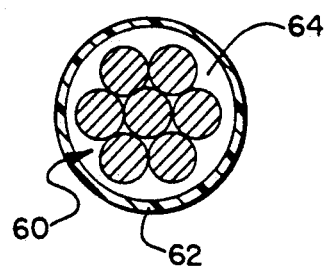
FIG. 6 is a cross-sectional view of an alternative embodiment of the lead body of FIG. 4.

FIG. 6 is a cross sectional view of an alternative embodiment of the lead body 11, having a conductor 60, and an insulation tubing 62 which surrounds the conductor 60 in a loose manner, with a spacial gap 64 formed in between. The thickness of the tubing 62 preferably ranges between 0.0020 inches to 0.0040 inches, and the average spacial gap 64 ranges from 0.0010 inches to 0.0020 inches. As a result, the overall outer diameter of the alternative embodiment of the lead body 11 ranges between 0.0080 inch to 0.0230 inch, and the preferred outer diameter of the lead body is 0.0130 inch.

One advantage of the alternative embodiment is to reduce the corrosion resulting from a pin hole in the lead body. If a pin hole were to develop in the tubing 62, the body fluid will leak through the tubing 62 inside the spacial gap 64. The leaking fluid will flow within the gap 64, to reduce the current density at the surface of the conductor 60, and to dilute the corrosive pH concentration on the surface of the conductor 60, thus substantially reducing corrosion.

Figure 7:
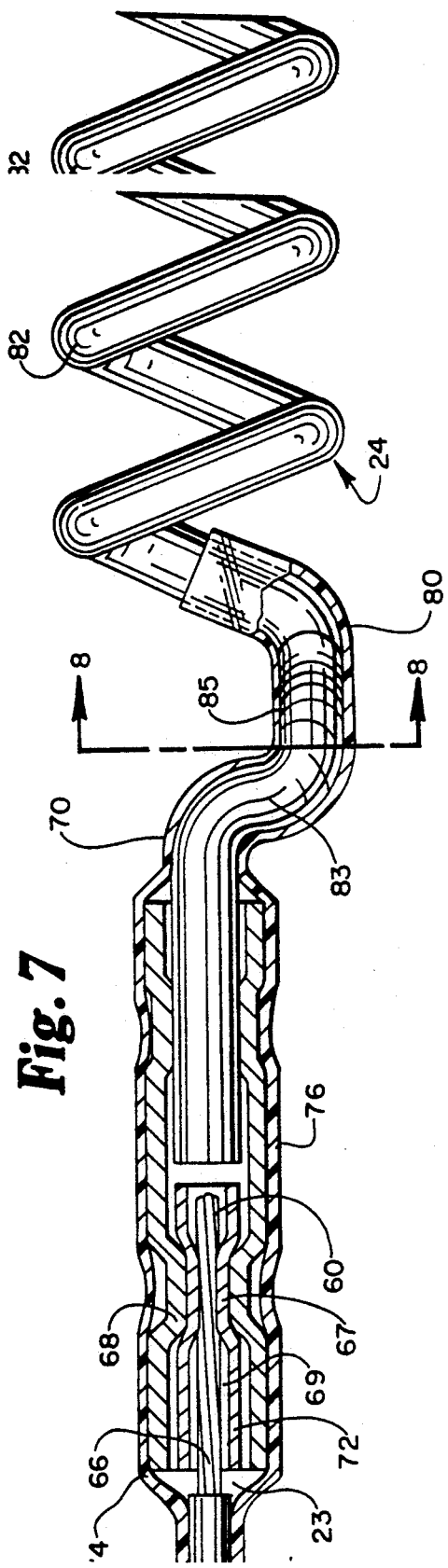
FIG. 7 is a greatly enlarged side elevational view of the distal end portion of the lead of FIGS. 2 and 3, with portions thereof cut away.

FIG. 7 is a greatly enlarged fragmentary side view of the distal end portion 70 of the lead 10. The distal end portion 70 includes the distal end portion 23 of the lead body 11, an adaptor sleeve 72, an outer sleeve 74, a sealant tubing 76 and the screw-type tip 24. The tip 24 serves a dual function, as an electrode tip and as a fixation device.

As discussed above, the conductor 60 has a significantly small outer diameter, which renders it somewhat difficult to be electrically connected to another conductor of larger outer diameter, such as the tip 24. The adaptor sleeve 72 is electrically conductive and is secured to the distal end 66 of the conductor 60 by conventional techniques, such as by means of a crimp 67.

The sleeve 72 is a short, generally pliable, hollow cylindrical tube with a central axial lumen 69 which extends throughout the axial length of the tube for accommodating the distal end 66 of the conductor 60. It should however be understood that the sleeve 72 can also be closed at one end and open at the opposite end. The sleeve 72 is made of stainless steel, such as 316L or 304L. The inner diameter of the sleeve 72 slightly exceeds the outer diameter of the conductor 60 in order to allow a close and possibly a friction fit connection therebetween. The sleeve 72 is about 0.0600 inches in length.

In the preferred embodiment, the outer diameter of the sleeve 72 is generally comparable in size to the outer diameter of the proximal end 71 of the tip 24, to facilitate the connection between the proximal end 71 of the tip 24 and the sleeve 72. In this respect, the proximal end 71 and the sleeve 72 are axially co-aligned and joined by means of an electrically conductive outer sleeve 74 of generally similar construction and design to the adaptor sleeve 72. A crimp 68 is formed to secure the outer sleeve 74 to the adaptor sleeve 72 and the conductor 60. Similarly, the outer sleeve 74 is crimped to the proximal end 71 of the tip 24.

An elongated generally cylindrical sealant tubing is heat shrunk around the distal end portion of the insulated conductor 60, the entire length of the outer sleeve 74, the proximal end portion 71 of the screw 24 and a crank portion 80 of the tip 24, for providing continuous insulation between the lead body 11 and the tip 24. The tubing 76 further acts as a sealant to prevent gross leakage of body fluids into the lead body 11. The sealant tubing is made of bio-compatible, bio-stable material such as Teflon ®, and has an outer diameter of approximately 0.03 inches.

Figure 8:
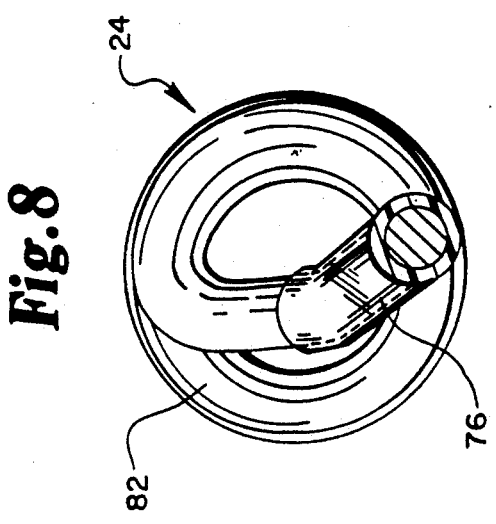
FIG. 8 is a greatly enlarged cross-sectional view of a screw tip, forming a part of the distal end portion of FIG. 7, taken along line 8—8.

Considering now the tip 24 in greater detail with respect to FIGS. 7 and 8, it is generally formed of the proximal end portion 71 which extends into the crank portion 80, which, in turn, extends into a coiled portion 82. The tip 24 is made of electrically conductive material used in conventional electrode pacing tips, and has a generally uniform and circular cross-section along its entire axial length. As indicated above, the outer diameter of the tip 24 is generally comparable to the outer diameter of the adaptor sleeve 72.

The proximal end portion 71 is elongated and measures approximately 0.0600 inches in length, and is axially aligned with the axis of symmetry of the coiled portion 82. The proximal end portion 71 extends into an angularly bent section 83 which forms a part of the crank portion 80. The bent section 83 extends into a loop 85 which is axially offset relative to the central axis of the coiled portion 82. Loop 85 will be described later in greater detail in connection with the introducer 40. The shaft 85 is designed to engage the introducer 40 to cause the entire lead 10 to rotationally advance or retract, while simultaneously providing over-perforation protection.

The shaft 85 is then bent and coiled to form the coiled portion 82, having a approximately 1½ to 3 turns, and having a pitch of approximately 1 mm (0.039 inch) per turn in axial length.

DESCRIPTION OF THE INTRODUCER

Referring now to the drawings and more particularly to FIGS. 2, 3, 9a, 9b and 17 thereof, the introducer 40 will now be described in detail. FIG. 2 is an exploded view of the lead system 30 and provides a side elevational view of the introducer 40. The introducer 40 is generally formed of a coupler 43 which engages the crank portion 80 of the tip 24 to cause it to rotate in the clockwise direction for engagement to the cardiac tissue 15, or in a counter-clockwise direction for dislodgement from the cardiac tissue 15. An elongated coiled body 44 is connected to the coupler 43 and gives the introducer 40 its flexible and torque transmitting characteristic.

The proximal end 42 of the coiled body 44 is coupled to a handle 45 which permits easier manipulation and rotation of the introducer 40. The handle 45 provides a diameter greater than the coil diameter to facilitate extension of the electrode 24 from the catheter 50 and to facilitate rotation to screw the electrode into the myocardium.

The coupler 43 will now be described in greater detail in relation to FIG. 9a which is a greatly enlarged side elevational view of the coupler 43. The coupler 43 includes an elongated cylindrical tubing 90 which is heat shrunk over a section of the coiled body 44 for insuring tight coupling. The tubing 90 is made of an electrically insulating material such as Teflon ® for isolating the coiled body of the introducer from the electrically conductive tip 24 of the lead 10. The tubing 90 has the following dimensions: approximately 0.3000 inches in length, 0.0500 inches outside diameter.

The tubing 90 has an aperture 92 which acts as an entranceway for the tip 24. The aperture 92 is longitudinal and is defined by a first edge 93 which extends along the axial direction, at a perpendicular angle to the outer contour 91 of the tubing 90. The first edge 93 is preferably 0.0400 inches in length, and extends into a second edge 94 which forms a slot about 0.02 inches wide. The second semicircular edge 94, in turn, extends into a third edge 95 which is generally parallel to the first edge 93 but is 0.0200 inches in length. The first, second and third edges 93, 94 and 95 form a retention section 98 which houses and firmly engages the crank portion 80 of the tip 24.

The third edge 95 extends into a ramp or sloped edge 96 which serves three functions, namely to help guide the crank portion 80 into the retention area 98, and to guide the tip out of the aperture 92. The third and more significant function of the ramp 96 is to prevent the tip 24 from over-perforating the cardiac tissue, as it will be explained later in connection with FIGS. 13 and 14. The ramp 96 is about 0.0700 inches in length and forms an angle of approximately 60° with the third edge 95.

The handle 45 is illustrated in FIG. 9b. As mentioned above, the handle 45 is functionally interchangeable with the coupler 43, thus allowing the tip 24 to engage, and the lead 10 to be assembled to the introducer 40 through either the coupler 43 or the handle 45.

The handle 45 includes a tip engaging portion 100 which couples with the tip 24 in a similar manner to the coupler 43. The tip engaging portion 100 includes an aperture 92 having similar shape and dimensions to the aperture 92 in the coupler 43. The tip engaging portion 100 is elongated and tubular, and is geometrically similar to coupler 43. While the tip engaging portion 100 can be made of the same insulation material as the tubing 90, it is also possible to select an electrically conductive material such as stainless steel.

Figure 3:
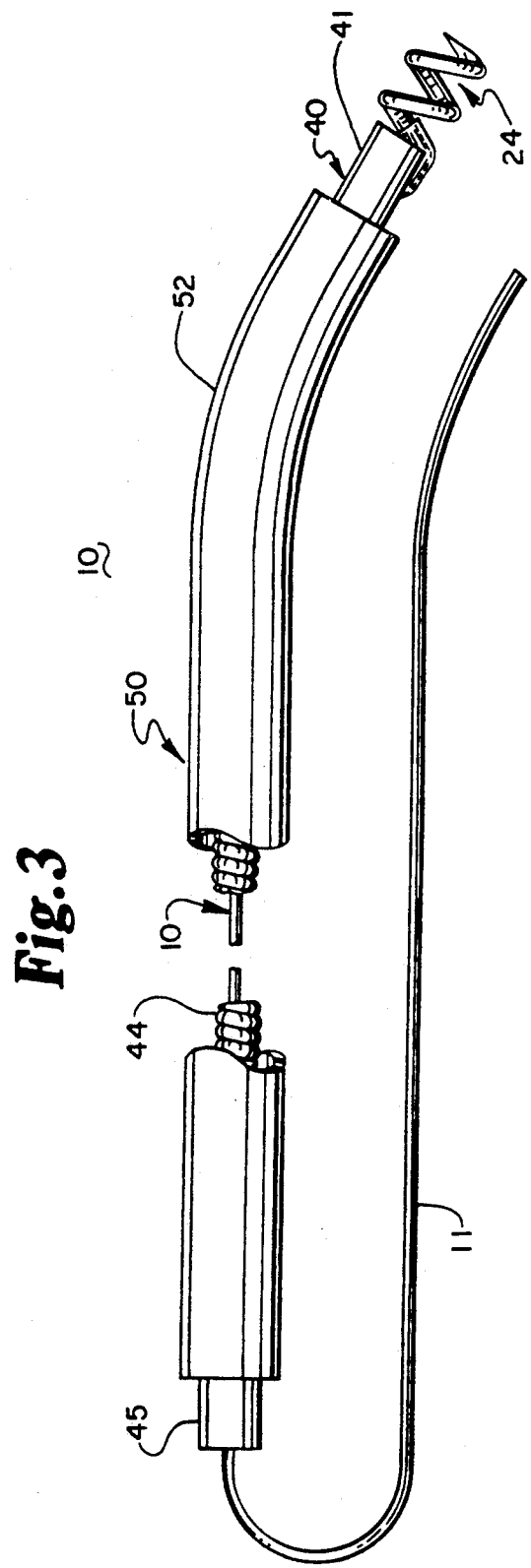
FIG. 3 is an isometric side elevational assembly view of the lead system of FIG. 2.

The handle 45 is insulated from the coiled body 44 by means of a neck portion 102, which imparts added flexibility to the coupler 45, and an added degree of movement to the introducer 40. It allows the lead tip to more easily follow relatively sharp bends in the catheter 50. The neck 102 is formed by positioning the proximal edge of the tip engaging portion 100 at a distance, such as 0.0900 inches from the distal tip of the coiled body 44, and by heat shrinking a tubing 104 across them. The tubing 104 is preferably made of heat shrinkable Teflon ® tubing and is about 0.5000 inches in length. The tubing 104 covers about seventy-five percent of the axial length of the tip engaging portion 100. The coiled body will now be described in greater detail in connection with FIGS. 2, 3 and 7. The coiled body shown in FIGS. 2 and 3 is a spring coil which transmits torque from one end to the other without significant loss. The coil is made of a single filar coil of 0.010 diameter wire. The number of filars and dimensions may be varied. The material may be MP35N, stainless steel or other metals. The wire is closely wound in abutting, identical, sequential coils to give the coiled body 44 a generally uniform outer diameter.

The coiled body 44 has an outer diameter of about 0.036 inches, and an overall axial length of 19.69 inches to 47.24 inches (50 cm to 120 cm). Therefore, when the lead 10 is assembled to the introducer 40, excess length of the lead body 11 protrudes outside the introducer 40, for connection to the connector block 27 of the pacemaker 26, as it will be clarified below in connection with FIGS. 15 and 16.

Figure 17:
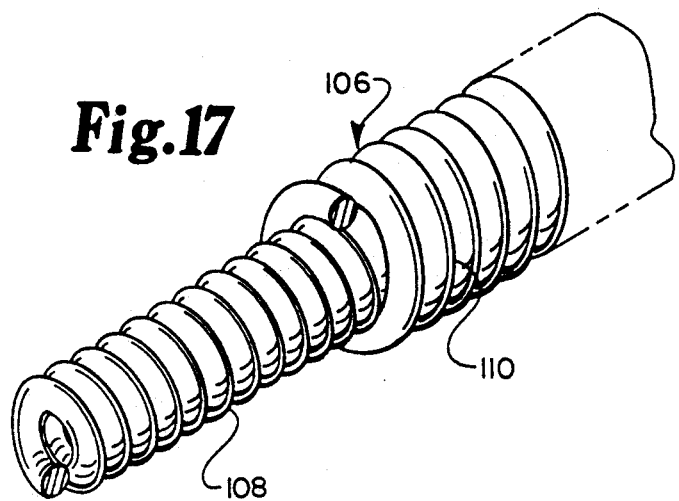
FIG. 17 is a greatly enlarged, fragmentary, isometric view of an alternative embodiment of the introducer shown in FIG. 2.

FIG. 17 is a greatly enlarged, isometric view of an alternative embodiment of the coiled body of the introducer 40. The coiled body 106 has similar composition and outer diameter to the coiled body 44. The coiled body 106 is formed of an inner coil 108 which is wound in one direction, and an outer coil 110 which is wound in the opposite direction. It should be understood that, while only two coils 108 and 110 are shown, an additional coil could also be added without departing from the scope of the present invention. Each additional coil is preferably wound in a direction opposite to that of the adjacent coils.

The inner coil 108 is generally wound in the clockwise direction while the outer coil 110 is wound in the counterclockwise direction, such that when a clockwise torque is applied to the coiled body 106, the inner coil 108 tends to expand, while the outer coil 110 tends to contract. This will increase the torsional stiffness of the introducer 40, while retaining its flexibility.

DESCRIPTION OF THE CATHETER

Referring now to the drawings and more particularly to FIGS. 2 and 3 thereof, the catheter 50 will now be described in detail. The catheter 50 is a conventional catheter sold under the tradename Sherpa ™ Guide Catheter by Medtronic, Inc., and is made of a layer of Teflon ® tubing and an outer layer of polyurethane tubing with braided stainless steel in between. The catheter 50 has a generally elongated tubular shape, and is about 23.62 inches (60 cm) in length. When the catheter 50 is assembled to the introducer 40, the handle 45 and a part of the introducer 40 protrudes outside the catheter 50 for manipulation. The catheter 50 has an inside diameter of 0.070 inches and an outside diameter of 0.0910 inches. Depending on the application, the catheter 50 can have a straight configuration, as shown in FIG. 2, or a curved shaped as shown in FIG. 3. It should however be appreciated that other shapes of the catheter 50, such as J shapes, are also envisaged within the scope of the present invention.

ASSEMBLY AND CONNECTION OF THE LEAD SYSTEM

The assembly and use of the lead system 30 will now be described in detail in relation to FIGS. 2, 3, 10 and 11. The lead system 30 is assembled along the assembly lines 111 and 112, as illustrated in FIG. 3, to yield the assembled lead system 30 shown in FIG. 3. The lead 10 is inserted inside, and pulled through the introducer 40, along the assembly line 111, until the distal end 41 of the introducer 40 firmly engages the screw-in tip 24. In this manner, a rotational torque imparted to the proximal end 42 is transmitted almost entirely to the tip 24. The lead-introducer assembly 30–40 is then inserted inside, and pulled through the catheter 50, along the assembly line 112.

Figure 10:
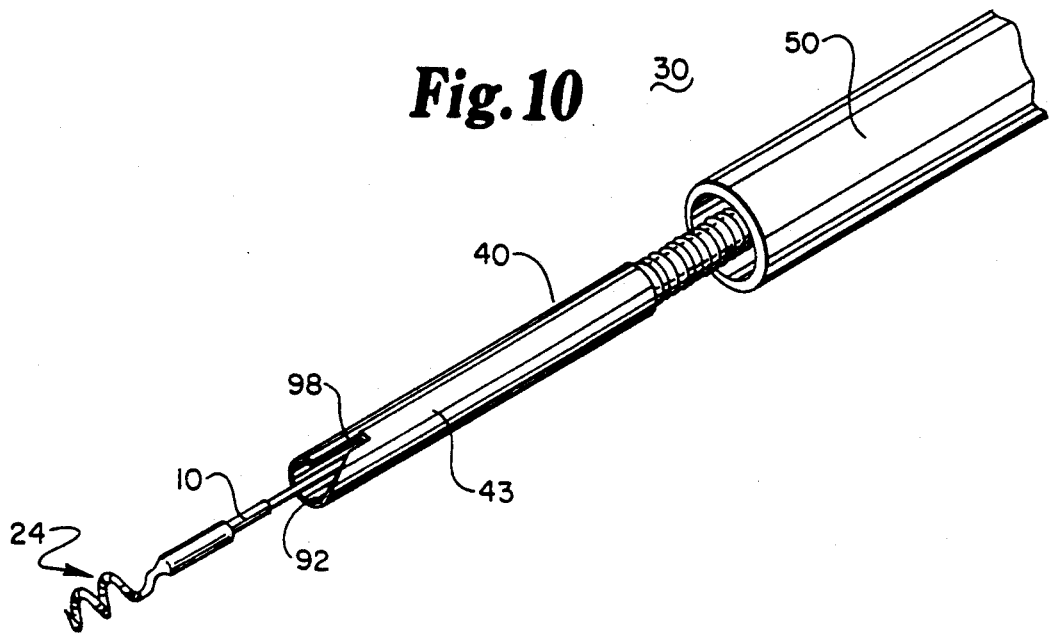
FIG. 10 is an enlarged fragmentary, isometric, assembly view of lead system of the present invention.
Figure 11:
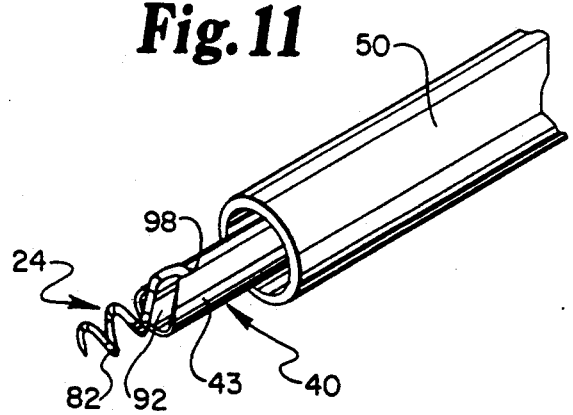
FIG. 11 is another enlarged view of the lead system shown in FIG. 2.

FIG. 10 is an exploded isometric view of the distal ends of the lead 10, the introducer 40 and the catheter 50 shown in an inter-engaged, partially assembled relationship. FIG. 11 is an exploded isometric assembly view of these distal ends, showing the crank portion 80 nesting in the retention section 98 of the aperture 92, with the coiled portion 82 of the tip 24 protruding outside the coupler 43.

During implantation, the tip 24 is recessed entirely within the catheter 50 to prevent contact with, and damage to the vessel 22 and the heart. When the distal end 52 of the catheter 50 is located in its approximate final placement position, the introducer 40 is pushed forward and the tip 24 is exposed and forced into contact with the cardiac wall 15. Whereupon, the introducer 40 is rotated clockwise and the resulting torque is transmitted to the coupler 43. The coupler 43, in turn, causes the tip 24 to rotate in the same direction, and to engage the cardiac tissue 15. This engagement action is illustrated in FIG. 12.

Figure 12:
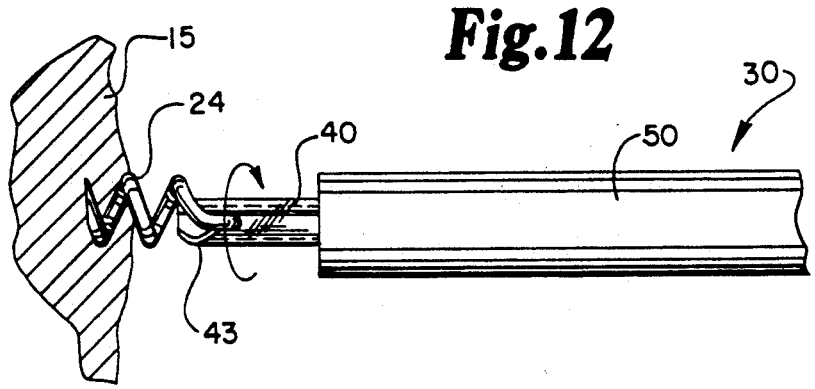
FIG. 12 is an enlarged, fragmentary, side elevational view of the lead system of FIGS. 10 and 11, showing the lead tip in the process of engaging the cardiac tissue.
Figure 13:
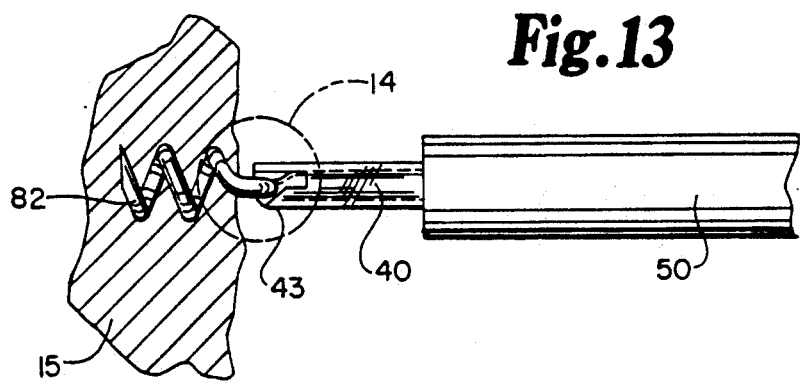
FIG. 13 is another enlarged view of the lead system of FIG. 12, shown completely inserted in the cardiac tissue.
Figure 14:
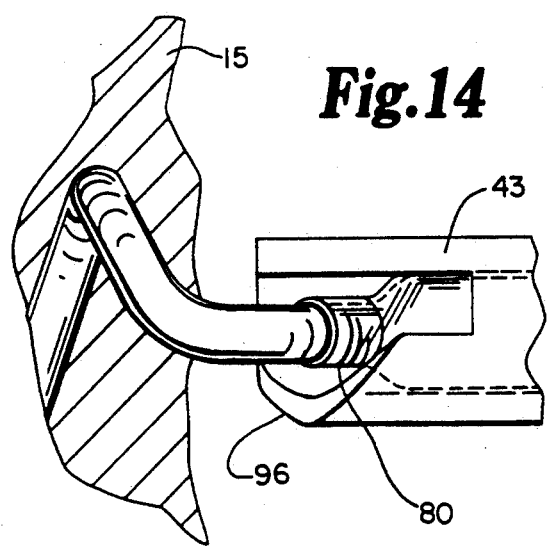

Referring now to FIGS. 12 and 13, over-perforation protection feature will now be described in greater detail. As the tip 24 is screwed deeper into the cardiac wall 15, it is pulled away from the coupler 43 in the direction of the cardiac wall 15 for further perforation and engagement. Simultaneously, the crank portion 80 rides on the ramp 96 and thus ceases rotation of the helix, thus preventing the tip 24 from being screwed further into the cardiac wall 15 regardless of the number of turns applied to the introducer 40. Consequently, the cardiac tissue 15 is protected from over-perforation. By selecting the pitch and number of coils in the coiled portion 82 of the tip 24, the electrode penetration depth can be prescribed. The depth of the aperture 123 can also be changed to control the penetration depth. It is possible to use the lead system 30 in various applications, including pediatric applications.

When the tip 24 is lodged in the cardiac wall 15, threshold tests are conducted to confirm the proper positioning of said lead 10. If adjustments are needed, the coupler 43 is advanced forward in contact with the crank portion 80, the introducer 40 is rotated in the counterclockwise direction in engagement with the tip 24. A continued counter-clockwise rotation of the introducer 40 will cause the tip 24 to be disengaged from the cardiac wall 15, and the tip 24 is repositioned and the threshold tests are repeated until satisfactory results are achieved.

Upon proper positioning of the lead 10, the catheter 50 and the introducer 40 are drawn back and retracted from the lead 10. The lead 10 is then cut to length and is connected to the pacemaker 26 via the converted connector block 27. Thus, the lead can be customized for length to suit each patient.

DESCRIPTION OF THE CONNECTOR BLOCK

The connector block 27 will now be described in greater detail in connection with FIGS. 15 and 16 of the drawings. One feature of the present lead system 30 is its adaptability for connection to a universal connector block, such as the IS-1 connector block shown in FIG. 1. It should be appreciated that the small size of the lead body 11 makes it difficult to connect the lead 10 to standard connectors without some modifications. It is the object of the present invention to minimize these modifications and the complexity of the connection process.

Figure 15:
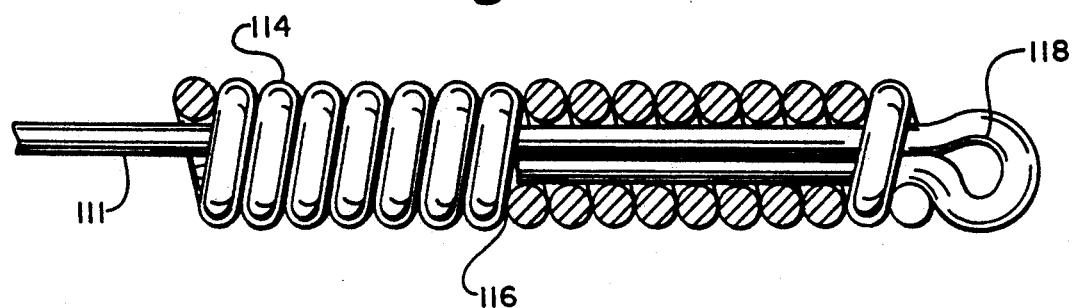
FIG. 15 is a greatly enlarged, fragmentary, partly sectional, side elevational view of the lead inserted in an adaptor coil for connection to a connector block.

FIG. 15 illustrates an adaptor coil 114 for use with the lead 10 to render it useable in standard IS-1 connector blocks. The adaptor coil 114 includes a standard coiled wire which is closely wound into helical loops, and has an inner diameter of about twice the outer diameter of the lead body, in order to allow easy insertion of the lead body therethrough. The inner diameter of the adaptor coil 114 can however be sufficiently large to accommodate the lead body, i.e. approximately as small as the outer diameter of the lead body 11. The outer diameter of the adaptor coil 114 is designed to fit into standard connector blocks.

Another advantage of the lead 10 is that the lead body is cut to length, thus avoiding the concerns associated with excess lead. When the lead body is cut to length, its end 116 is inserted inside, pulled through and fed back into the adaptor coil 114, to form a loop 118 for better retention, and to keep the lead 10 from slippage during insertion into the connector block 27. Other retention means, such as a knot, are also useable to prevent the lead 10 from slipping back through the adaptor coil 114.

The adaptor coil-lead assembly 114-10 is inserted into the connector block 27. A set screw 120 compresses a portion of the adaptor coil-lead assembly 114-10 and causes the adaptor coil 114 to crush the insulation of the insulation coating 61 of the lead body 11, and therefore to expose the conductor 60. As a result, the lead 10 is now mechanically and electrically connected to the pacemaker. The current pathway is from the feedthrough of the pacemaker, through the connector block 127 and setscrew 120 to the lead conductor 60.

ALTERNATIVE EMBODIMENTS

Figure 18:
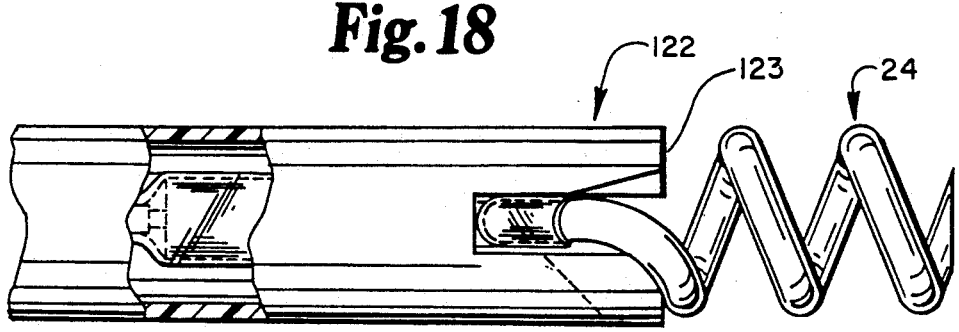
FIG. 18 is an enlarged, fragmentary, partly sectional, side elevational view of an alternative embodiment of the coupler.

It should become apparent to those skilled in the art after reviewing the present specification that alternative embodiments are covered by the scope of the inventive lead system 30. Some of these embodiments will be described in connection with FIGS. 18, 19, 20, 21 and 22. FIG. 18 illustrates an alternative coupler 122. The coupler 122 is similar in every respect to the coupler 43, with the exception that it includes two symmetrical and diametrically opposed apertures 123 and 124.

Figure 19:
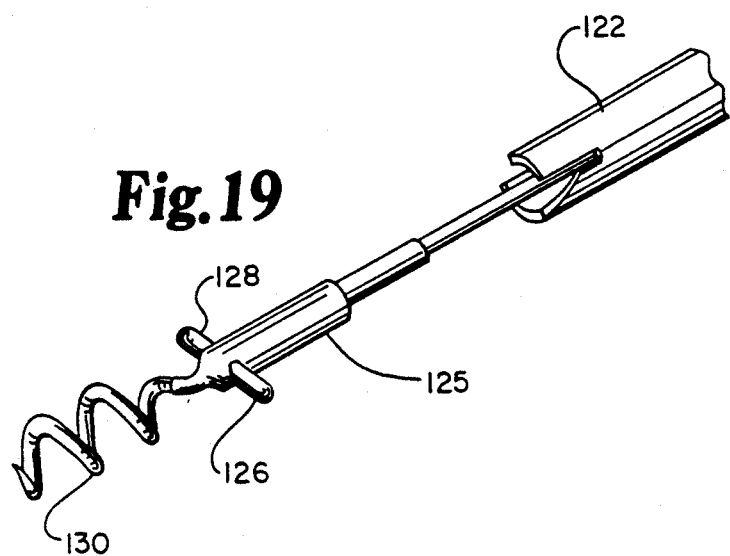
FIG. 19 is an enlarged, fragmentary, isometric assembly view of an alternative embodiment of the lead system according to the present invention.

FIG. 19 illustrates an alternative distal end portion 125, which is similar to the distal end portion 70 of the lead 10, as illustrated in FIG. 7, with the difference that it includes two symmetrical and diametrically opposed lateral pins 126 and 128. These pins 126 and 128 engage the apertures 123 and 124 of the coupler 122, shown in FIG. 18, for causing the screw tip 130 to engage the cardiac wall 15. The dual pin configuration 126, 128 replaces the crank portion 80.

Figure 20:
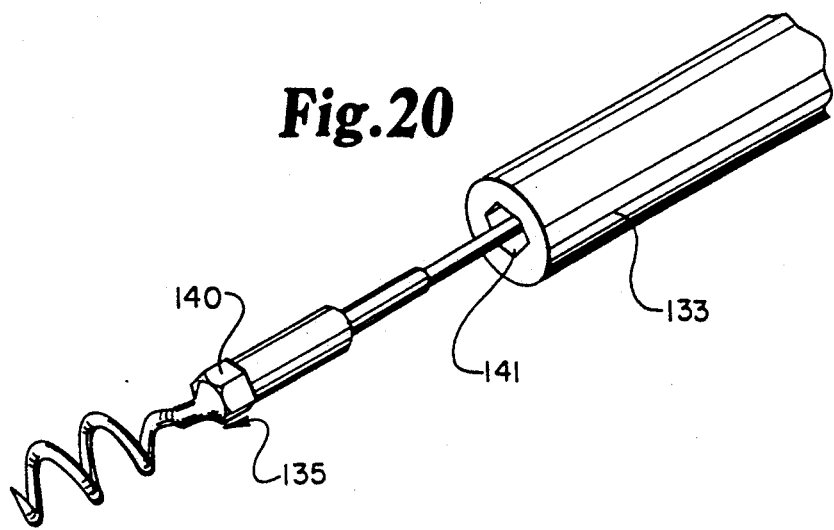
FIG. 20 is an enlarged, fragmentary, isometric assembly view of another alternative embodiment of the lead system according to the present invention.

FIG. 20 illustrates another alternative coupler 133 and distal end portion 135. The distal end 135 has a nut 140 which fits in a hex nut portion 141 in the coupler 133 for coupling therewithin.

Figure 21:
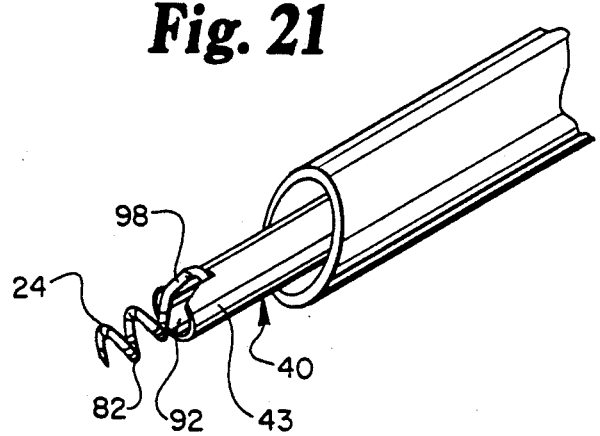
FIG. 21 is an enlarged, fragmentary side elevational view of a further alternative embodiment of the lead system according to the present invention, showing a coupler section mounted on the a catheter.

FIG. 21 illustrates a new catheter design which includes a catheter 143 having a catheter body 145 ending in a coupler 147. The catheter body 145 is tubular and is similar in design and construction to the catheter 50. The catheter body 143 terminates in, or is alternatively connected to, the coupler 147. The coupler 147 has a similar design to either the coupler 43 or the coupler 122 (FIG. 18). The new catheter 143 allows for a further miniaturization of the lead system 30, in that it is now possible to dispense with the introducer 40. In general, the outer diameter of the catheter 143 is about equal to the outer diameter of the introducer 40, and even smaller for special applications.

In neurological or other applications where it is desirable to "inject" the lead 10 transcutaneously, the lead 10 is introduced into a needle 150 which houses the tip 24 during insertion into the body. Once the needle 150 is properly positioned, the catheter 143 is pushed forward for causing the tip 24 to engage the adjacent tissue, such as the muscle (not shown), and the lead 10 is engaged into the tissue as discussed above in connection with the preferred embodiment of the lead system 30. Once the tests are completed, the catheter 143 is rotated in the counter-clockwise direction for connection with the tip 24 and for causing it to disengage from the tissue in which it was lodged.

In certain applications it would be possible to force medication inside the space 155 formed between the lead 10 and the catheter 143. In other applications, the catheter 143 is retracted, and the lead 10 is cut, capped and stored underneath the skin.

Figure 22:
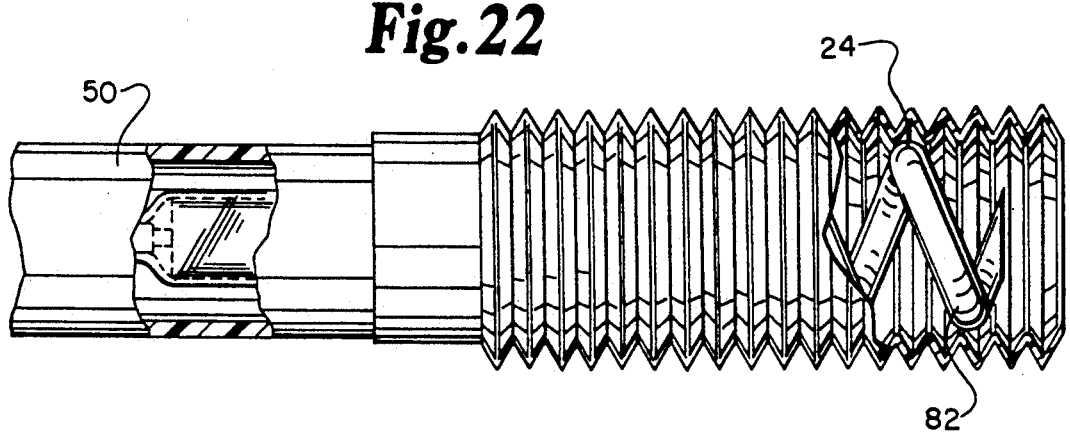
FIG. 22 is an enlarged, fragmentary side elevational view of an alternative embodiment of the lead system of FIG. 21, including a flexible corrugated section for housing the lead tip.
Figure 15:
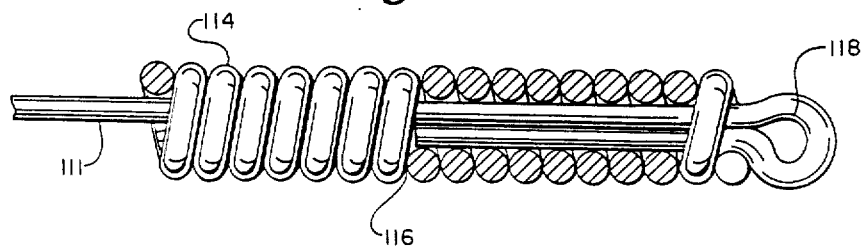
Figure 16:
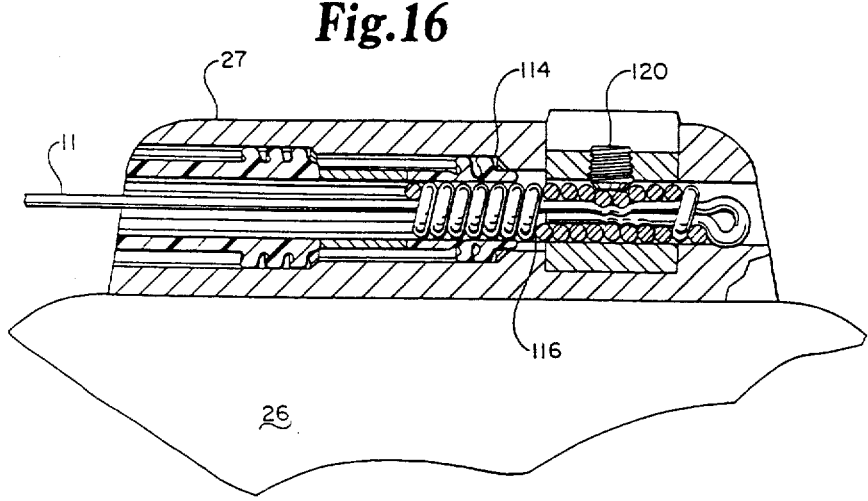

FIG. 22 illustrates yet another application for the catheter 143. A catheter assembly 156 is illustrated for use in cardiac pacing. In this respect, it would not be completely desirable to use the catheter 143 illustrated in FIG. 21 for cardiac implantation, because the tip 24 is exposed and might cause some damage to the vessel 22 or the heart valve. Consequently, the catheter assembly 156 is designed to address this concern.

The catheter assembly 156 includes a catheter 157 which is similar in design and construction to the catheter 143. The catheter assembly 156 also includes a flexible, bellow type, corrugated tip protection section 158 which covers the tip 24 during implantation, and which folds as the catheter assembly 156 is forced against the cardiac wall 15. It should be understood that other applications for the catheter 143 and the catheter assembly 156 are also foreseeable.

While particular embodiments of the present invention have been disclosed, it is to be understood that various different modifications are possible and are contemplated within the scope of the specification, drawings, abstract and appended claims.

What is claimed is:

1. A lead system for connecting a source of electrical energy to a human or animal body tissue, the system comprising:
   a. a lead having:
      (1) a proximal end and a distal end, said distal end including fixation means for engaging the body tissue, said fixation means including a helical tip for engaging the body tissue and means for connecting said tip to a lead body; and
      (2) said lead body extending between said proximal end and said distal end, whereby said lead body includes a conductor formed of a plurality of infinitesimal, bio-compatible electrically conductive strands tightly bundled in a cable-like fashion, said lead body further including a dielectric bio-compatible insulation coating which surrounds said conductor to provide an insulation layer between said conductor and the body, said connecting means including an electrically conductive sleeve means for coupling said tip to said conductor and sealant means, surrounding at least said conductive sleeve means, for insulating it;
(b) introducer means for assembly with, and for receiving said lead, said introducer means having:
  (1) a body member, extending between a proximal end and a distal end of said introducer means, for transmitting torque from said introducer means proximal end to said introducer means distal end; and
  (2) coupler means, secured to said introducer means distal end, for engaging said fixation means and for controlling its engagement to the body tissue; and
(c) catheter, for telescopically receiving said introducer means, to impart stiffness and improved steerability to said lead.

2. The lead system as defined in claim 1, wherein said conductive sleeve includes:
  a. an electrically conductive adaptor sleeve which is connected to an exposed section of said conductor; and
  b. an outer sleeve for interconnecting said exposed section to said tip.

3. The lead system as defined in claim 2, wherein said sealant means includes a bio-compatible tubing which is heat shrunk around a distal end portion of said conductor, said outer sleeve, and a proximal end portion of said tip, for providing a fluid tight sealant to prevent body fluids from seeping into said lead body.

4. The lead system as defined in claim 1, wherein said coupler means includes an elongated, generally cylindrical tip engaging member which is tightly connected to a section of said body member, such that said tip engaging member has a dielectric composition for insulating said body member from said fixation means;
  wherein said fixation means includes a tip having:
    a. a proximal end portion which extends into a crank portion for engaging said coupler means of said introducer means; and
    b. a coiled portion wound around a geometric central axis for engaging the body tissue; and
  wherein said tip engaging member includes an aperture which acts as an entranceway for said tip, and which retains and firmly engages said crank portion, for causing it to rotate in a first predetermined direction for engagement to the body tissue, or in a second direction for dislodgement from the body tissue.

5. A lead system for connecting a source of electrical energy to a human or animal body tissue, the system comprising:
  a. a lead having:
    (1) a proximal end and a distal end, said distal end including fixation means for engaging the body tissue, said fixation means including a tip having a proximal end portion which extends into a crank portion and a coiled portion wound around a geometric central axis for engaging the body tissue; and
    (2) a lead body extending between said proximal end and said distal end, said lead body including an elongated insulated conductor;
  b. introducer means for assembly with, and for receiving said lead, said introducer means having:
    (1) a body member, extending between a proximal end and a distal end of said introducer means, for transmitting torque from said introducer proximal end to said introducer distal end; and
    (2) coupler means, secured to said introducer means distal end, for engaging said fixation means and for controlling its engagement to the body tissue, said coupler means including an elongated, generally cylindrical tip engaging member which is tightly connected to a section of said body member, such that said tip engaging member has a dielectric composition for insulating said body member from said fixation means, said tip engaging member including an aperture which acts as an entranceway for said tip, and which retains and firmly engages said crank portion, for causing it to rotate in a first predetermined direction for engagement to the body tissue, or in a second direction for dislodgement from the body tissue; and
  c. catheter, for telescopically receiving said introducer means, to impart stiffness and improved steerability to said lead.

6. The lead system as defined in claim 5, wherein said tip is electrically conductive and is used as a tip electrode.

7. The lead system as defined in claim 5, wherein said aperture is defined by a retention area for engaging said crank portion, and a ramp which helps to guide said crank portion into said retention area, to guide said tip out of said aperture, and to prevent said tip from overperforating the body tissue.

8. The lead system as defined in claim 7 wherein said coupler includes a second aperture which is similar to, and diametrically opposed to said coupler aperture.

9. A lead system for connecting a source of electrical energy to a human or animal body tissue, including a connector means for connection of said source of electrical energy to a lead, the system comprising:
  a. a lead having:
    (1) a proximal end and a distal end, said distal end including fixation means for engaging the body tissue; and
    (2) a lead body extending between said proximal end and said distal end, said lead body including an elongated conductor;
  b. introducer means for assembly with, and for receiving said lead, said introducer means having:
    (1) a body member, extending between a proximal end and a distal end of said introducer means, for transmitting torque from said introducer proximal end to said introducer distal end; and
    (2) coupler means, secured to said introducer means distal end, for engaging said fixation means and for controlling its engagement to the body tissue;
  c. catheter, for telescopically receiving said introducer means, to impart stiffness and improved steerability to said lead; and
  wherein said connector means further includes adaptor means, connected to said lead body, for rendering it useable in standard connector blocks.

10. A lead system for connecting a source of electrical energy to a human or animal body tissue, the system comprising:
  a. a lead having:
    (1) a proximal end and a distal end, said distal end including fixation means for engaging the body tissue, said lead fixation means including a tip having a coiled portion wound around a geometric central axis for engaging the body tissue and two similar, and symmetrically and diametrically opposed lateral pins; and (2) a lead body extending between said proximal end and said distal end, said lead body including an elongated insulated conductor;

b. introducer means for assembly with, and for receiving said lead, said introducer means having:

(1) a body member, extending between a proximal end and a distal end of said introducer means, for transmitting torque from said introducer proximal end to said introducer distal end; and (2) coupler means, secured to said introducer means distal end, for engaging said fixation means and for controlling its engagement to the body tissue, said coupler means including an elongated, generally cylindrical tip engaging member which is tightly connected to a section of said body member, such that said tip engaging member has a dielectric composition for insulating said body member from said fixation means, said coupler including first and second diametrically opposed apertures for engaging said two lateral pins for causing said tip to engage the body tissue, wherein each of said first and second apertures is defined by a retention area for engaging a said lateral pin, and a ramp which helps to guide said lateral pin into said retention area, to guide said tip out of said aperture, and to prevent said tip from over-perforating the body tissue; and c. catheter, for telescopically receiving said introducer means, to impart stiffness and improved steerability to said lead.

11. A lead system for connecting a source of electrical energy to a human or animal body tissue, the system comprising:

a. a lead having:

(1) a proximal end and a distal end, said distal end including fixation means for engaging the body tissue, said fixation means including a tip having a coiled portion wound around a geometric central axis for engaging the body tissue and a hex-nut for mating with a socket aperture, to cause said tip to engage the body tissue; and (2) a lead body extending between said proximal end and said distal end, said lead body including an elongated insulated conductor;

b. introducer means for assembly with, and for receiving said lead, said introducer means having:

(1) a body member, extending between a proximal end and a distal end of said introducer means for transmitting torque from said introducer proximal end to said introducer distal end; and (2) coupler means, secured to said introducer means distal end, for engaging said fixation means and for controlling its engagement to the body tissue, said coupler means including an elongated, generally cylindrical tip engaging member which is tightly connected to a section of said body member, such that said tip engaging member has a dielectric composition for insulating said body member from said fixation means, said coupler means further including a hex-nut like socket aperture for engaging said lead fixation means; and c. catheter, for telescopically receiving said introducer means, to impart stiffness and improved steerability to said lead.

12. A lead system for connecting a source of electrical energy to a human or animal body tissue, the system comprising:

a. a lead having:

(1) a proximal end and a distal end, said distal end including fixation means for engaging the body tissue, said fixation means including a tip having a coiled portion wound around a geometric central axis for engaging the body tissue and means for receiving torque comprising a projection extending away from said coiled portion; and (2) a lead body extending between said proximal end and said distal end, said lead body including an elongated, insulated conductor;

b. introducer means for assembly with, and for receiving said lead, said introducer means having:

(1) a body member, extending between a proximal end and a distal end of said introducer means, for transmitting torque from said introducer proximal end to said introducer distal end; and (2) coupler means, secured to said introducer means distal end, for engaging said fixation means and for controlling its engagement to the body tissue, said coupler means including an elongated, generally cylindrical tip engaging member which is tightly connected to a section of said body member, said tip engaging member including an aperture which acts as an entranceway for said tip, and which retains and firmly engages said projection, for causing it to rotate in a first predetermined direction for engagement to the body tissue, or in a second direction for dislodgement from the body tissue, said aperture defined by a retention area for engaging said projection and a ramp which helps to guide said projection into said retention area, to guide said tip out of said aperture, and to prevent said tip from over-perforating the body tissue.

13. The lead system as defined in claim 5 or claim 12, further including handle means connected to said introducer proximal end, for easier manipulation and rotation of said introducer body member.

14. The lead system as defined in claim 13, wherein said handle means has a generally similar construction to said coupler means, such that said handle means and coupler means are functionally interchangeable.

15. The lead system as defined in claim 14, wherein said handle means includes:

a. a tip engaging portion for engaging said tip crank portion; and b. a dielectric tubing for connecting said tip engaging portion to said introducer body member;

and wherein said tubing forms a neck portion which separates said body member from said handle tip engaging portion, for imparting greater movement flexibility to said introducer.

16. The lead system as defined in claim 15, wherein said tip engaging portion is electrically conductive.

17. A lead system according to claim 12 wherein said tip includes a crank portion, and wherein said projection comprises said crank portion.

18. A lead system according to claim 12 wherein said projection comprises a lateral pin.

19. A lead system according to claim 5 or claim 12 wherein said elongated conductor comprises a plurality of infinitesimal, bio-compatible electrically conductive strands tightly bundled in a cable-like fashion.

20. A lead system according to claim 19 wherein said conductor includes a central strand and a plurality of peripheral strands.

21. A lead system according to claim 5 or claim 12 wherein said conductor extends linearly along said the length of said lead body.

22. A lead system according to claim 5 or claim 12 wherein said lead body comprises insulative tubing, surrounding said conductor in a loose manner, with a spatial gap formed therebetween.

23. The lead system as defined in claim 5 or 12, wherein said body member includes at least a first elongated, closely wound spring coil.

24. The lead system as defined in claim 23, wherein said first coil has an outer diameter of about 0.0360 inches, and an axial length of 19.69 inches to 47.24 inches (50 cm to 120 cm), shorter than the length of said lead body, such that when said lead is assembled to said introducer excess length of said lead body protrudes outside said introducer body member.

25. The lead system as defined in claim 24, wherein said body member includes a second elongated, closely wound spring coil which is formed concentrically and coaxially with said first spring coil, and
wherein said second coil spring is wound in the opposite direction to the winding direction of said first coil spring, such that when clockwise torque is applied, said first spring coil tends to contract, while said second spring coil tends to expands, for increasing the torsional stiffness of said introducer.

26. The lead system as defined in claim 12, wherein the source of electrical energy includes a connector means for connection to said lead body; and
wherein said connector means includes adaptor means, connected to said lead body, for rendering it useable in standard connector blocks.

27. The lead system as defined in claim 1 or claim 26, wherein said adaptor means includes a helically wound coil, having an inner lumen for accommodating said proximal end of said lead body, and wherein said adaptor means fits in standard connector blocks.

* * * * *

UNITED STATES PATENT AND TRADEMARK OFFICE
CERTIFICATE OF CORRECTION

PATENT NO. : 5,246,014
DATED : September 21, 1993
INVENTOR(S) : Williams et al.

Figure 16:
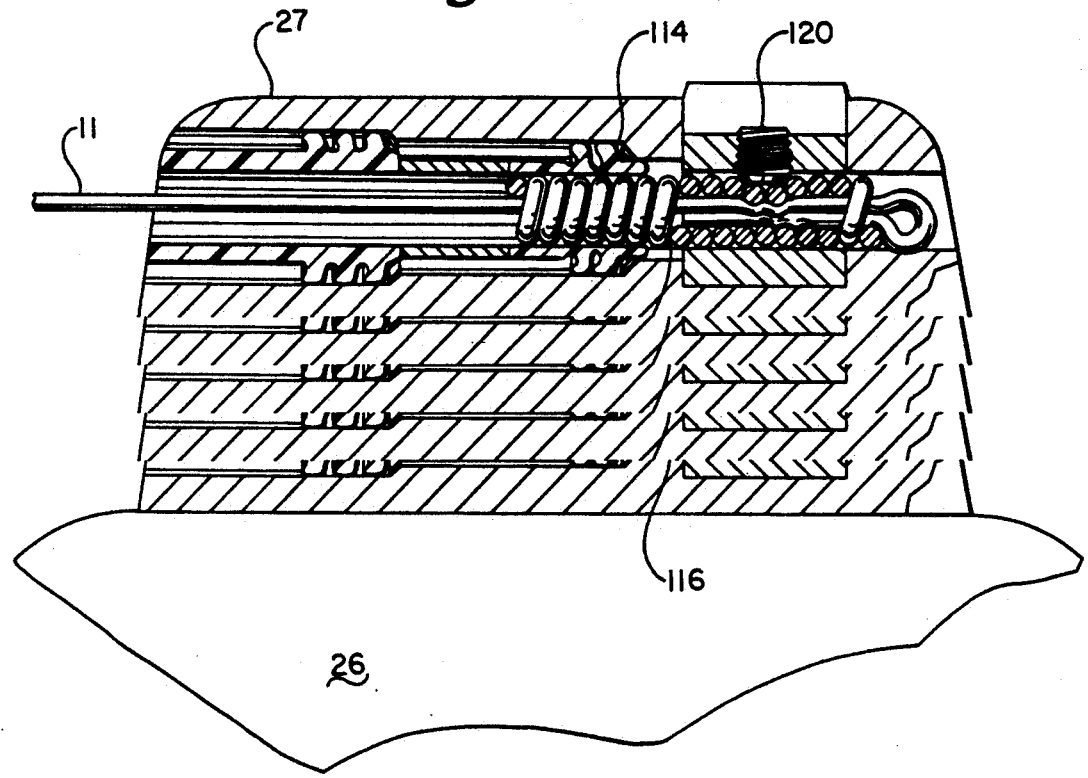
FIG. 16 is an enlarged cross-sectional side elevational view of the lead and the adaptor coil of FIG. 15, shown connected to a connector block.

It is certified that error appears in the above-indentified patent and that said Letters Patent is hereby corrected as shown below:

The drawing sheet, consisting of Figs. 15 and 16, should be deleted to be replaced with the drawing sheet, consisting of Figs. 15 and 16, as shown on the attached page.

Signed and Sealed this

Twenty-sixth Day of July, 1994

Attest:

BRUCE LEHMAN

Attesting Officer     Commissioner of Patents and Trademarks